(12) United States Patent
Seitz

(10) Patent No.: US 9,394,564 B2
(45) Date of Patent: Jul. 19, 2016

(54) POLYNUCLEOTIDE AMPLIFICATION

(75) Inventor: Alexander Seitz, Vienna (AT)

(73) Assignee: LEXOGEN GMBH, Vienna (AT)

(*) Notice: Subject to any disclaimer, the term of this patent is extended or adjusted under 35 U.S.C. 154(b) by 1217 days.

(21) Appl. No.: 12/095,485

(22) PCT Filed: Nov. 29, 2006

(86) PCT No.: PCT/AT2006/000494
 § 371 (c)(1),
 (2), (4) Date: Sep. 19, 2008

(87) PCT Pub. No.: WO2007/062445
 PCT Pub. Date: Jun. 7, 2007

(65) Prior Publication Data
 US 2009/0311754 A1    Dec. 17, 2009

(30) Foreign Application Priority Data
 Nov. 29, 2005  (AT) .................................. 1923/2005
 Nov. 29, 2006  (WO) ................. PCT/AT2006/000494

(51) Int. Cl.
 *C12Q 1/68*    (2006.01)

(52) U.S. Cl.
 CPC ............ *C12Q 1/6809* (2013.01); *C12Q 1/6844* (2013.01); *C12Q 1/6853* (2013.01)

(58) Field of Classification Search
 None
 See application file for complete search history.

(56) References Cited

U.S. PATENT DOCUMENTS

| | | | |
|---|---|---|---|
| 5,932,451 A | 8/1999 | Wang et al. | |
| 5,962,272 A | 10/1999 | Chenchik et al. | |
| 6,114,149 A * | 9/2000 | Fry et al. ...................... | 435/91.2 |
| 6,270,966 B1 * | 8/2001 | Weinstein et al. ........... | 435/6.12 |
| 6,287,825 B1 | 9/2001 | Weissman et al. | |
| 6,558,927 B1 | 5/2003 | Mueller et al. | |
| 6,632,641 B1 * | 10/2003 | Brennan et al. .................... | 506/9 |
| 2001/0053519 A1 * | 12/2001 | Fodor et al. ........................ | 435/6 |
| 2002/0012922 A1 | 1/2002 | Hilbush et al. | |
| 2002/0177701 A1 | 11/2002 | Weissmann et al. | |
| 2003/0108874 A1 | 6/2003 | Kane et al. | |
| 2004/0166499 A1 | 8/2004 | Hayashizaki | |

FOREIGN PATENT DOCUMENTS

| | | |
|---|---|---|
| EP | 1 186 673 A | 3/2002 |
| EP | 1 369 480 A | 12/2003 |
| WO | 93/18176 A | 9/1993 |
| WO | 96/40998 A1 | 12/1996 |
| WO | 02/065093 A | 8/2002 |
| WO | 03/035841 A | 5/2003 |
| WO | WO 03035841 A2 * | 5/2003 |

OTHER PUBLICATIONS

Amara, R. R., et al., "Specific polyadenylation and purification of total messenger RNA from *Escherichia coli*," Nucleic Acids Research (1997), 25:3465-3470.

Barnes, W. M., "PCR amplification of up to 35-kb DNA with high fidelity and high yield from A bacteriophage templates," Proc Natl Acad Sci USA (1994), 91:2216-2220.

Behr, S., et al., "A fully automated multicapillary electrophoresis device for DNA analysis," Electrophoresis (1999), 20:1492-1507.

Carninci, P., et al., "Thermostabilization and thermoactivation of thermolabile enzymes by trehalose and its application for the synthesis of full length cDNA," Proc Natl Acad Sci USA (1998), 95:520-524.

Clark, J.M., "Novel non-templated nucleotide addition reactions catalyzed by procaryotic and eucaryotic DNA polymerases," Nucl Acids Res (1988), 16:9677-9686.

Di Giusto, D. A., et al., "Strong positional preference in the interaction of LNA oligonucleotides with DNA polymerase and proofreading exonuclease activities: implications for genotyping assays," Nucl Acids Res (2004), 32:e32.

Frohman, M.A., et al., "Rapid production of full-length cDNAs from rare transcripts: Amplification using a single gene-specific oligonucleotide primer," Proc Natl Acad Sci USA (1988), 85:8998-9002.

Furuichi, Y., et al., "A blocked structure at the 5' terminus of mRNA from cytoplasmic polynedrosis virus," Nature (1975), 253:374-375.

Gunderson, K. L., et al., "Decoding Randomly Ordered DNA Arrays," Genome Research (2004), 14:870-877.

Hawkins, P. R., et al. "Full-Length cDNA Synthesis for Long-Distance RT-PCR of Large mRNA Transcripts," BioTechniques (2003), 34:768-773.

Heller, C., et al., "Robust Field Inversion Capillary Electrophoretic Separation of Long DNA Fragments," Meth Mol Biol (2001), 162:293-305.

Irie, T., et al., "Automated DNA fragment collection by capillary array gell electrophoresis in search of differentially expressed genes," Electrophoresis (2000), 21:367-374.

Jin, Y., et al., "Nontemplated nucleotide addition prior to polyadenylation: A comparison of *Arabidopsis* cDNA and genomic sequences," RNA (2004), 10:1695-1697.

Kovarova, M., et al., "Nontemplated nucleotide addition prior to polyadenylation: A comparison of *Arabidopsis* cDNA and genomic sequences," Nucl Acids Res (2000), 28:e70.

Liang, P., et al., "Differential Display of Eukaryotic Messenger RNA by Means of the Polymerase Chain Reaction," Science (1992), 257:967-971.

(Continued)

*Primary Examiner* — Prabha Chunduru

(74) *Attorney, Agent, or Firm* — Chainey P. Singleton; Edwin S. Flores; Chalker Flores, LLP

(57) ABSTRACT

The present invention provides a method for amplifying a pool of polynucleotide molecules in a sample, characterized by the steps of a) obtaining a sample or RNA and reverse transcription of entire RNA molecules thus creating full length cDNA or obtaining a sample of full length cDNA, b) tailing the 3' end of the transcribed cDNA with a polynucleotide tail after the 3' end, c) amplification of the cDNA using a pair of primers, wherein a first 3' primer is specific for the 5' end of the cDNA and a second 5' primer is specific for the a upstream portion of the polynucleotide tail and the next 1 to 10 nucleotides upstream of the 3'polynucleotide tail of the cDNA.

21 Claims, 4 Drawing Sheets

(56) References Cited

OTHER PUBLICATIONS

Figure 1:
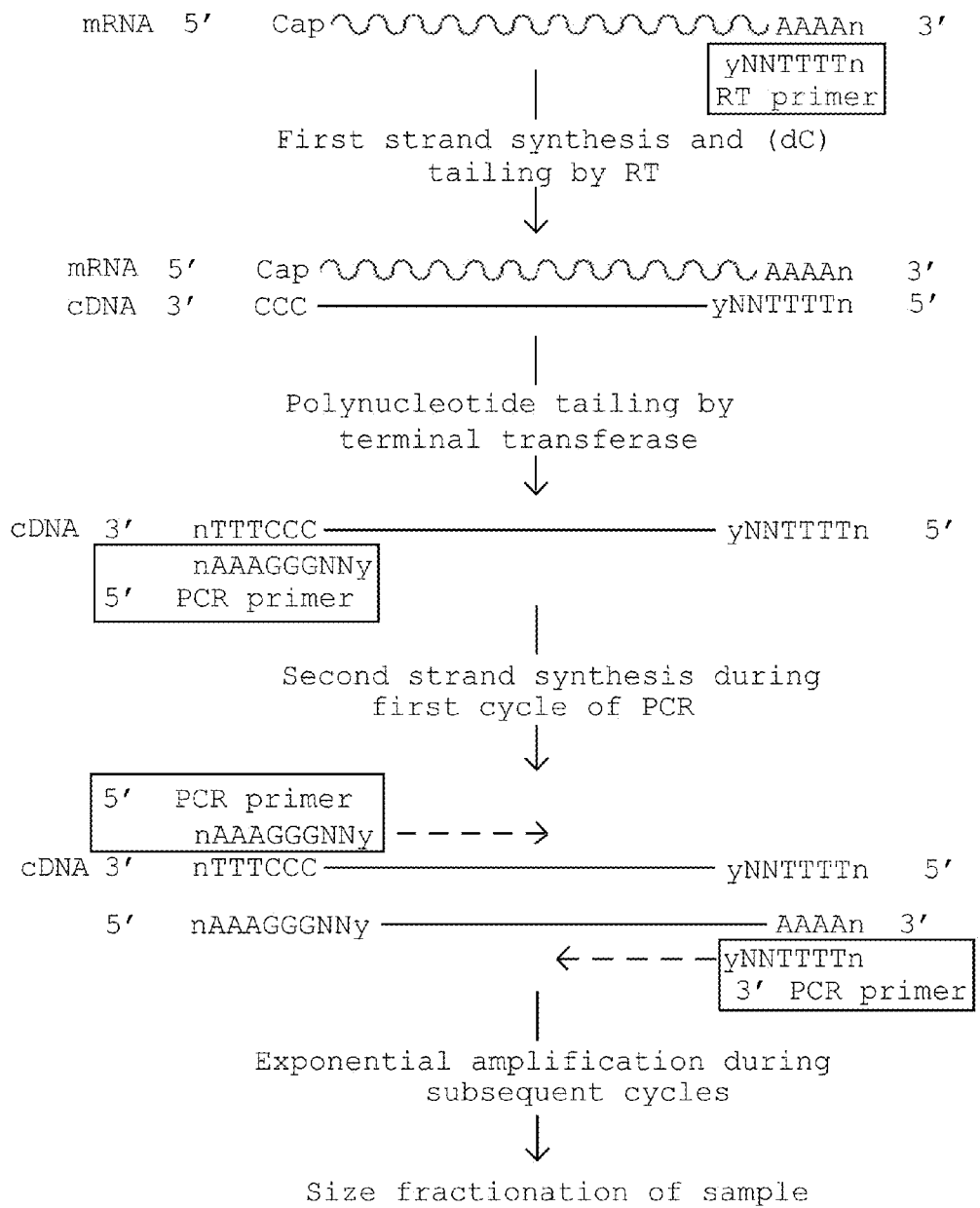

Magnusdottir, S., et al., "Collection of Capillary Electrophoresis Fractions on a Moving Membrane," Meth Mol Biol (2001), 162:323-331.

Matz, M., et al., "Ordered differential display: a simple method for systematic comparison of gene expression profiles," Nuc Acids Res (1997), 25:2541-2542.

Mizuno, Y., et al., "Increased specificity of reverse transcription priming by trehalose and oligo-blockers allows high-efficiency window separation of mRNA display," Nuc Acids Res (1999), 27:1345-1349.

Morris, M. D., et al., "Pulsed-Field Capillary Electrophoresis Separation of Large DNA Fragments," Meth Mol Biol (2001), 162:307-321.

Prashar, Y., et al., "Analysis of differential gene expression by display of 3' end restriction fragments of cDNAs," Proc Natl Acad Sci USA (1996), 93:659-663.

Prashar, Y., et al., "reads: a Method for Display of 3'-End Fragments of Restriction Enzyme-Digested cDNAs for Analysis of Differential Gene Expression," Meth Enzymol (1999), 303:258-272.

Rebagliati, M. R., et al., "Identification and Cloning of Localized Maternal RNAs from Xenopus Eggs," Cell (1985), 42:769-777.

Schmidt, W. M., et al., "CapSelect: A highly sensitive method for 5' Cap-dependent enrichment of full-length cDNA in PCR-mediated analysis of mRNAs," Nuc Acids Res (1999), 27:e31.

Spiess, A.-N., et al., "A Highly Efficient Method for Long-Chain cDNA Synthesis Using Trehalose and Betaine," Anal Biochem (2002), 301:168-174.

Skerra, A., "Phosphorothioate primers improve the amplification of DNA sequences by DNA polymerases with proofreading activity," Nuc Acids Res (1992), 20:3551-3554.

Thiel, V., et al., "Effective Amplification of 20-kb DNA by Reverse Transcription PCR," Anal Biochem (1997), 252:62-70.

Welsh, J., et al., "Arbitrarily primed PCR fingerprinting of RNA," Nuc Acids Res (1992), 20:4695-4970.

Wittwer, C. T., et al., "Continuous Fluorescence Monitoring of Rapid Cycle DNA Amplification," BioTechniques (1997), 22:130-138.

Wittwer, C. T., et al., "The LightCyclerÔ: A Microvolume Multisample Fluorimeter with Rapid Temperature Control," BioTechniques (1997), 22:176-181.

Xie, W., et al., "Microchip-Based Capillary Electrophoresis Systems," Meth Mol Biol (2001), 162:67-83.

Yang, H.-L., et al., "High fidelity PCR with an off/on switch mediated by proofreading polymerases combining with phosphorothioate-modified primer," Biochem Biophy Res Comm (2005), 328:265-272.

\* cited by examiner

SEQUENCE LISTING

<160> NUMBER OF SEQ ID NOS: 34

<210> SEQ ID NO 1
<211> LENGTH: 7
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (7)..(7)
<223> OTHER INFORMATION: n is a, c, g, or t

<400> SEQUENCE: 1 acacacn                                                           7

<210> SEQ ID NO 2
<211> LENGTH: 7
<212> TYPE: DNA
<213> ORGANISM: Artificial
<220> FEATURE:
<223> OTHER INFORMATION: primer

<400> SEQUENCE: 2 acacaca                                                           7

```
<210> SEQ ID NO 3
<211> LENGTH: 7
<212> TYPE: DNA
<213> ORGANISM: Artificial
<220> FEATURE:
<223> OTHER INFORMATION: primer

<400> SEQUENCE: 3 acacacc                                                                    7

<210> SEQ ID NO 4
<211> LENGTH: 7
<212> TYPE: DNA
<213> ORGANISM: Artificial
<220> FEATURE:
<223> OTHER INFORMATION: primer

<400> SEQUENCE: 4 acacact                                                                    7

<210> SEQ ID NO 5
<211> LENGTH: 7
<212> TYPE: DNA
<213> ORGANISM: Artificial
<220> FEATURE:
<223> OTHER INFORMATION: primer

<400> SEQUENCE: 5 acacacg                                                                    7

<210> SEQ ID NO 6
<211> LENGTH: 17
<212> TYPE: DNA
<213> ORGANISM: Artificial
<220> FEATURE:
<223> OTHER INFORMATION: RNA-terminus

<400> SEQUENCE: 6
gatatccgcc ctgtgct                                                         17

<210> SEQ ID NO 7
<211> LENGTH: 17
<212> TYPE: DNA
<213> ORGANISM: Artificial
<220> FEATURE:
<223> OTHER INFORMATION: RNA-terminus

<400> SEQUENCE: 7
ctgtgggcaa ggtctca                                                         17

<210> SEQ ID NO 8
<211> LENGTH: 17
<212> TYPE: DNA
<213> ORGANISM: Artificial
<220> FEATURE:
<223> OTHER INFORMATION: RNA-terminus

<400> SEQUENCE: 8
tgtccctttt ggtccca                                                         17

<210> SEQ ID NO 9
<211> LENGTH: 17
<212> TYPE: DNA
<213> ORGANISM: Artificial
<220> FEATURE:
<223> OTHER INFORMATION: RNA-terminus
```

<400> SEQUENCE: 9
ttgtggaagg gctcgca                                                    17

<210> SEQ ID NO 10
<211> LENGTH: 17
<212> TYPE: DNA
<213> ORGANISM: Artificial
<220> FEATURE:
<223> OTHER INFORMATION: RNA-terminus

<400> SEQUENCE: 10
cgatgccccc attcaca                                                    17

<210> SEQ ID NO 11
<211> LENGTH: 17
<212> TYPE: DNA
<213> ORGANISM: Artificial
<220> FEATURE:
<223> OTHER INFORMATION: RNA-terminus

<400> SEQUENCE: 11
caccaccatg gatctga                                                    17

<210> SEQ ID NO 12
<211> LENGTH: 17
<212> TYPE: DNA
<213> ORGANISM: Artificial
<220> FEATURE:
<223> OTHER INFORMATION: RNA-terminus

<400> SEQUENCE: 12
caacgggaag cctctaa                                                    17

<210> SEQ ID NO 13
<211> LENGTH: 17
<212> TYPE: DNA
<213> ORGANISM: Artificial
<220> FEATURE:
<223> OTHER INFORMATION: RNA-terminus

<400> SEQUENCE: 13
acgacccctt catctta                                                    17

<210> SEQ ID NO 14
<211> LENGTH: 17
<212> TYPE: DNA
<213> ORGANISM: Artificial
<220> FEATURE:
<223> OTHER INFORMATION: RNA-terminus

<400> SEQUENCE: 14
gatatgatgc gcaaagg                                                    17

<210> SEQ ID NO 15
<211> LENGTH: 17
<212> TYPE: DNA
<213> ORGANISM: Artificial
<220> FEATURE:
<223> OTHER INFORMATION: RNA-terminus

<400> SEQUENCE: 15
gacatggcct aagcaag                                                    17

```
<210> SEQ ID NO 16
<211> LENGTH: 17
<212> TYPE: DNA
<213> ORGANISM: Artificial
<220> FEATURE:
<223> OTHER INFORMATION: RNA-terminus

<400> SEQUENCE: 16
gagatgagca cggaagc                                                  17

<210> SEQ ID NO 17
<211> LENGTH: 17
<212> TYPE: DNA
<213> ORGANISM: Artificial
<220> FEATURE:
<223> OTHER INFORMATION: RNA-terminus

<400> SEQUENCE: 17
gaaatccgct ttgattt                                                  17

<210> SEQ ID NO 18
<211> LENGTH: 17
<212> TYPE: DNA
<213> ORGANISM: Artificial
<220> FEATURE:
<223> OTHER INFORMATION: RNA-terminus

<400> SEQUENCE: 18
ggtatcagct ccccatc                                                  17

<210> SEQ ID NO 19
<211> LENGTH: 17
<212> TYPE: DNA
<213> ORGANISM: Artificial
<220> FEATURE:
<223> OTHER INFORMATION: RNA-terminus

<400> SEQUENCE: 19
gctatgggcc tgggtca                                                  17

<210> SEQ ID NO 20
<211> LENGTH: 17
<212> TYPE: DNA
<213> ORGANISM: Artificial
<220> FEATURE:
<223> OTHER INFORMATION: RNA-terminus

<400> SEQUENCE: 20
gttatgggcg gagtgga                                                  17

<210> SEQ ID NO 21
<211> LENGTH: 22
<212> TYPE: DNA
<213> ORGANISM: Artificial
<220> FEATURE:
<223> OTHER INFORMATION: primer

<400> SEQUENCE: 21
agagattttt tttttttttt ga                                            22

<210> SEQ ID NO 22
<211> LENGTH: 20
<212> TYPE: DNA
<213> ORGANISM: Artificial
<220> FEATURE:
<223> OTHER INFORMATION: Primer
```

```
<400> SEQUENCE: 22
agagattttt tttttttttg                                             20

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
agagattttt tttttttttg c                                           21

<210> SEQ ID NO 24
<211> LENGTH: 22
<212> TYPE: DNA
<213> ORGANISM: Artificial
<220> FEATURE:
<223> OTHER INFORMATION: Primer

<400> SEQUENCE: 24
agagattttt tttttttttt gt                                          22

<210> SEQ ID NO 25
<211> LENGTH: 22
<212> TYPE: DNA
<213> ORGANISM: Artificial
<220> FEATURE:
<223> OTHER INFORMATION: Primer

<400> SEQUENCE: 25
agagattttt tttttttttt ca                                          22

<210> SEQ ID NO 26
<211> LENGTH: 22
<212> TYPE: DNA
<213> ORGANISM: Artificial
<220> FEATURE:
<223> OTHER INFORMATION: Primer

<400> SEQUENCE: 26
agagattttt tttttttttt ag                                          22

<210> SEQ ID NO 27
<211> LENGTH: 23
<212> TYPE: DNA
<213> ORGANISM: Artificial
<220> FEATURE:
<223> OTHER INFORMATION: Primer

<400> SEQUENCE: 27
agagattttt tttttttttt taa                                         23

<210> SEQ ID NO 28
<211> LENGTH: 21
<212> TYPE: DNA
<213> ORGANISM: Artificial
<220> FEATURE:
<223> OTHER INFORMATION: Primer

<400> SEQUENCE: 28
aaaaaaaaaa aaaagggat a                                            21
```

```
<210> SEQ ID NO 29
<211> LENGTH: 21
<212> TYPE: DNA
<213> ORGANISM: Artificial
<220> FEATURE:
<223> OTHER INFORMATION: Primer

<400> SEQUENCE: 29
aaaaaaaaaa aaaaagggac a                                              21

<210> SEQ ID NO 30
<211> LENGTH: 21
<212> TYPE: DNA
<213> ORGANISM: Artificial
<220> FEATURE:
<223> OTHER INFORMATION: Primer

<400> SEQUENCE: 30
aaaaaaaaaa aaaaagggag a                                              21

<210> SEQ ID NO 31
<211> LENGTH: 21
<212> TYPE: DNA
<213> ORGANISM: Artificial
<220> FEATURE:
<223> OTHER INFORMATION: Primer

<400> SEQUENCE: 31
aaaaaaaaaa aaaaagggaa a                                              21

<210> SEQ ID NO 32
<211> LENGTH: 21
<212> TYPE: DNA
<213> ORGANISM: Artificial
<220> FEATURE:
<223> OTHER INFORMATION: Primer

<400> SEQUENCE: 32
aaaaaaaaaa aaaaagggt a                                               21

<210> SEQ ID NO 33
<211> LENGTH: 21
<212> TYPE: DNA
<213> ORGANISM: Artificial
<220> FEATURE:
<223> OTHER INFORMATION: Primer

<400> SEQUENCE: 33
aaaaaaaaaa aaaaagggct a                                              21

<210> SEQ ID NO 34
<211> LENGTH: 21
<212> TYPE: DNA
<213> ORGANISM: Artificial
<220> FEATURE:
<223> OTHER INFORMATION: Primer

<400> SEQUENCE: 34
aaaaaaaaaa aaaaagggtt a                                              21
```

POLYNUCLEOTIDE AMPLIFICATION

The present invention relates to the field of specific polynucleotide amplification.

To understand the causalities of the different states life presents itself, one needs to find the factors and processes that lead to it. One central element in this quest is the genome where information is stored in such a fashion that it can be propagated through the generations in a highly conserved manner. In executing the information contained in the genome, DNA is transcribed into RNA and further translated into protein. Studying the genome (DNA), transcriptome (RNA) and proteome (protein) has in recent years greatly contributed to our understanding of the molecular basis of life.

An array of possibilities exists to compare RNA samples in vitro. An early approach is the method of differential hybridization or differential screening (Rebagliati et al., 1985). It involves picking at random clones (or sequences) from cDNA libraries and checking for their presence in different concentration in samples of RNA. An enormous effort has to be put into identifying a single differentially expressed transcript as their population is thought to be below 1%. Subtractive hybridization has been proposed to overcome this problem by enriching for differentially expressed transcripts prior to screening. Another way of addressing the problem of abundance was made by introducing high-density micro arrays. In using micro array technology 100s to 1000s of cDNAs, corresponding to RNAs of genes of interest, are spotted and bound onto a surface. They are normally derived from sequenced EST libraries and—if non redundant—can cover as many transcripts as spots fit onto the membrane. In short, RNA extracted from cells or tissues of interest are labeled, e.g. during reverse transcription, and hybridized to these microarrays. The signal intensity of corresponding spots between two or more RNA preparations can then be compared. Even though this technology has produced massive amounts of data, there are two fundamental drawbacks of all these hybridization techniques. One is cross hybridization. This means that two DNA molecules do not need to be complementary over their entire sequence to hybridize. Therefore this introduces ambiguity towards the identity of the molecule that hybridizes (binds) to the spot. Secondly one can only compare molecules that have been spotted, limiting the search to sequences that are present in the library used to generate the array.

An alternative approach was introduced in 1992 (Liang et al., 1992; Welsh et al., 1992) that today is generally known as "differential display" (DD). In DD the total mRNAs population of a sample is first divided into defined pools of cDNAs during reverse transcription (RT). This is accomplished by priming the RT with one, two or x base anchored oligo dT primers, subdividing the samples into 3, 12 or $3\times4^{x-1}$ fractions. These anchor bases hybridize to the bases immediately upstream of the poly A tail. Therefore selecting for mRNA molecules to be reverse transcribed whose bases immediately upstream of the poly A tail are complementary to the anchor bases of the primer. In a subsequent Polymerase chain reaction (PCR) arbitrary primers and anchored primers are used to amplify defined pools of cDNA. Corresponding pools are run side by side on a gel that separates them by size. Differences of expression levels are reflected in differences in band intensity. Bands of interest are cut out of the gel, reamplified and sequenced. One drawback of the original DD is that it uses arbitrary primers for amplification. Such a shotgun approach can reach full transcriptome coverage only statistically, by covering the transcriptome several times. Therefore some RNA molecules will necessarily be presented several times in the display and others might not be present at all.

Recently methods have been introduced that amplify pools of RNA in a more systematic fashion (Prashar et al., 1996; Prashar et al., 1999). In principle, three additional steps are involved. After first strand cDNA synthesis second strand synthesis carried out to get double stranded DNA that can be cut with a restriction enzyme. In a third step an adaptor is ligated to the 5' ends of the fragments. These fragments are then PCR amplified with one primer being complementary to the 5' adaptor sequence and an anchor primer that was used for RT. It was estimated by the authors that each 6-base cutting restriction enzyme cuts 8% of the cDNAs at a position between 50 and 400 bases from the 3' poly A tail of the mRNA. Therefore more than 12 restriction enzymes will be necessary to approach a complete coverage of the transcriptome. A somewhat more elegant variety of this method was described by Matz et al. (1997) with the introduction of "ordered differential display" that takes advantage of the PCR suppression effect.

However, besides covering the transcriptome only statistically at one level or another, all afore mentioned DD methods suffer from another drawback. They will give the investigator only part of the mRNA sequence that is differentially expressed. Downstream of these DD technologies one will still have to either screen cDNA libraries or where available online sequence libraries for full length clones or employ methodologies that can discover 5' and 3' sequences from a partially known mRNA sequence such as RACE (Frohman et al., 1988). Even identifying such full length transcripts will still not yield certainty at least in eukaryotes that the mRNA found is the mRNA that generated the signal as in eukaryotes a major contributor to genome complexity is splicing. Therefore the sequence found on the display can be common to several splice variants. Furthermore different splice variants of a gene may have different functions, making it highly desirable to know the correct splice variant that generated the signal.

A goal of the present invention is to provide a method that can amplify (enrich for) defined subpopulations of transcripts in their entire length with full coverage of all mRNA molecules present in the sample.

The present invention now provides a method for amplifying a pool of polynucleotide molecules in a sample, characterized by the steps of:
  a) obtaining (or providing) a sample of RNA and reverse transcription of entire RNA molecules thus creating full length cDNA or obtaining (or providing) a sample of full length cDNA,
  b) tailing the 3' end of the transcribed cDNA with a polynucleotide tail after the 3' end,
  c) amplification of the cDNA using a pair of primers, wherein a first (3') primer is specific for the 5' end of the cDNA and a second (5') primer is specific for the upstream portion of the polynucleotide tail and the next 1 to 10 nucleotides (i.e. the next 1 or 2, 3, 4, 5, 6, 7, 8, 9 or 10 nucleotides), preferably 1 to 5 nucleotides, even more preferred 3 to 5 nucleotides, upstream of the 3' polynucleotide tail of the cDNA. Of course the second primer can also comprise more specific nucleotides further upstream of the 1 to 10 nucleotide region upstream of the tail specific region (complement).

A full length cDNA can be created by a reverse transcription process described below, or by methods known in the state of the art. Methods to generate full length cDNA are abundantly known to the skilled man in the art, e.g. disclosed in U.S. Pat. No. 5,962,271 and U.S. Pat. No. 5,962,272. Such generated cDNA can also be used as starting material to pool full-length cDNA into different fractions. These methods use the template switching ability of reverse transcriptase to add a defined sequence to the 5' end of the cDNA in a cap dependent manner. The primer that is needed in the subsequent amplification will therefore have a portion that will be complementary to the so generated 3' end of the cDNA and will define what fraction of cDNA will be amplified through several, e.g. 1 to 10, additional bases defined by the 5' end of the mRNA molecules amplified.

Therefore it is preferred that a tail is added to the cDNA by the template switching ability of the reverse transcriptase, preferably in a cap dependent manner and the second amplification primer (5' primer) comprises complementary nucleotides to the so added tail and oligo-dCs and 1 to 10 nucleotides upstream of the oligo-dC sequence.

As used herein, the term "reverse transcriptase" relates to any polymerase that has reverse transcriptase activity and can be used to synthesize cDNA from RNA.

As used herein, the term "full length cDNA" is defined as DNA that includes a sequence complementary to the RNA sequence from the first base to the last base of the RNA. In case of RNA molecules that have a cap and/or a polyA tail as is the case for e.g. most eukaryotic mRNA, "full length cDNA" is defined as DNA that includes a sequence complementary to the RNA sequence from the first base after the cap, e.g. the RNA 7-methylguanosine cap or RNA m7G cap, to the last base before the poly A tail of the RNA used as a template.

As used herein, the term "full length amplification product" is defined as DNA that includes a sequence complementary to the RNA sequence from the first base to the last base of the RNA. In case of RNA molecules that have a cap and/or a polyA tail as is the case for e.g. most eukaryotic mRNA, "full length amplification product" is defined as amplification product that includes a sequence complementary to the RNA sequence from the first base after the cap to the last base before the poly (A) tail of the RNA used as a template.

A central element of this invention is the fact that full length RNA molecules can be represented in subpopulations that are defined on their 5' and/or 3' end. In principle that means that after the generation of full length cDNA by any means known in the art, the 5' and/or 3' sequence can be used to formulate a set of primer combinations (primer matrix) that has the following quality.

1) Each cDNA will be amplified by only one primer pair in the absence of miss priming. Therefore full transcriptome coverage can be reached without redundancy.
2) Each cDNA sequence within such a defined pool will encode the full amino acid sequence of the protein translated from the corresponding RNA and also
3) Define its transcription start site on its gene (there could be different RNA molecules transcribed from the same gene that can have different transcription start sites).

In comparing quality (1) to original DD one can state that therein the arbitrary primers have the property of either not being complementary to a specific cDNA, being complementary once or being complementary more than once. Therefore each cDNA can be represented either not at all, or once or more than once. When using alternative methodologies that include a restriction enzyme, each restriction enzyme will cut a specific cDNA either not at all or once or more than once. Therefore truly complete transcriptome coverage can never be reached. And increasing the probability for mRNAs to be represented at least one time in the display will mean to increase redundancy.

Qualities (2) and (3) can also not be reached by differential display techniques used to date without employing downstream technologies such as RACE.

The present invention provides methods for amplifying and analyzing the transcriptome through qualitative and quantitative detection of differentially expressed RNA molecules. The technique according to the invention is an organized full length expression display.

In a preferred embodiment the method according to the invention comprises a primer, which is specific for the (preferably 3' poly A) tail of the RNA or mRNA and the next 1 to 10 nucleotides, preferably 1 to 5 nucleotides, even more preferred 3 to 5 nucleotides, upstream of the (poly A) tail, that is used for the reverse transcription and/or one amplification primer is specific for a corresponding (5' poly-T) stretch of the cDNA, which is complementary to the (3' poly A) tail of the RNA or mRNA, and the next 1 to 10 nucleotides, preferably 1 to 5 nucleotides, even more preferred 3 to 5 nucleotides, downstream of the corresponding (5' poly-T) stretch of the cDNA. Accordingly in addition to the selective 3' primer described above a selective 5' primer can be used to increase the selective power of the primer pair and thus increase the number of cDNA pools defined by the specific nucleotides next to the end sequence anchors.

Preferably the primer for reverse transcription consists of deoxynucleotides.

Generally, the primers throughout this specification can be of any nucleotides, such as deoxyribonucleotides or ribonucleotides. Although deoxynucleotides are preferred in most cases, ribonucleotide primers are also feasible. Therefore a deoxyribonucleotide in a given primer, such as given in examples below, may be substituted by one of its ribonucleotide analogue (e.g. dG by G, dA by A, dC by C, dT by T or U) or other nucleotide analogues.

Preferably the tailing of the 3' end is performed using terminal transferase. —Although other tailing methods are also disclosed, like ligation of a tail sequence, which can be e.g. a defined arbitrary sequence. The terminal transferase can add a certain number of nucleotides preferably uniformly selected from one nucleotide type. Any other means for tailing, adding a tail sequence can also be used, e.g. employing the template switching ability of the reverse transcriptase or by ligating the tail sequence which can be uniformly of one type of nucleotides or of varying nucleotides. Such a tail is preferably a sequence in the range between 5 and 500 nucleotides, more preferred less than 400, less than 300, less than 200, less than 100, less than 50 or less than 30 nucleotides.

In a preferred embodiment the amplification of the cDNA sequences using a selective primer pair is performed by PCR. PCR or polymerase chain reaction is a well established technique known in the state of the art to amplify polynucleotides using a polymerase, nucleotidetriphosphates, primers, buffer substances and cofactors such as Mg ions and a temperature protocol for hybridization, polymerisation and melting or strand separation.

Preferably the first primer and/or second primer for the amplification consists of deoxynucleotides.

In a preferred embodiment the method according to the invention comprises an additional step of separation of the amplification products according to their length. The separation of the created polynucleotides renders a characterization, isolation and sequence determination possible for each pool after the selective polymerisation which allows a significant advantage for this preferred embodiment in practice.

Preferably the separation is performed by gel electrophoresis, preferably agarose gel electrophoresis, polyacrylamide gel electrophoresis, or capillary electrophoresis.

Even more preferred the method according to the invention comprises an additional step of determining the identity or sequence of the amplification products. Sequence determination can be done for example by gel sequencing, e.g. PCR with dideoxynucleotides, or in an automated sequencer.

Preferably the step of determining the identity or sequence of the amplification products is performed by an automated process on a chip.

The sample used for reverse transcription preferably contains total RNA or mRNA, preferably purified RNA or mRNA, from a specimen. Total RNA includes, but is not limited to, protein coding RNA also called coding RNA such as messenger RNA (mRNA) and non protein coding RNA (non coding RNA or ncRNA), such as ribosomal RNA (rRNA), transfer RNA (tRNA), micro RNA (miRNA), small interfering RNA (siRNA), piwi-interacting RNA (piRNA), small nuclear RNA (snRNA) and small nucleolar RNA (snoRNA). Every one of these classes, alone or together with one or more classes, can be analysed according to methods that are within the scope of the invention.

These RNA molecules are preferably purified by affinity chromatography using e.g. an oligo-dT-cellulose column. Thus mRNA with a poly A tail can be preselected.

It is preferred in the inventive method that reverse transcription is carried out at high stringency conditions to increase selectivity of the anchored primers, which can be used as a pool of anchored primers in one polymerisation reaction, as well as separate primers for different polymerisation reactions. In the present invention the phrases "stringent hybridization conditions" or "stringent conditions" refer to conditions under which a primer of the invention will hybridize to its target sequence, but to a minimal number of other sequences. High stringency can be achieved for example by using a high annealing temperature alone or in combination with a chemical additive such as dimethylsulfoxide (DMSO), formamide, tetramethylammonium chloride (TMAC) and Tetramethylammonium oxalate (TMAO) (Kovarova et al. 2000). Examples for high stringency hybridization conditions are given in Sambrook et al., Molecular Cloning: A Laboratory Manual (Cold Spring Harbor Laboratory, N.Y. 1989) and Ausubel et al., Current Protocols in Molecular Biology, Greene Publishing Assoc. and Wiley and Sons, N.Y. 1994. Under standard PCR conditions often an annealing temperature is chosen that is about 5 degree Celsius below the melting temperature of the primer. Keeping reaction conditions constant the melting temperature in turn is mainly dependent on the length and the GC-content of the oligonucleotides, which can be calculated by common means known in the art. Under more stringent conditions the annealing temperature is raised above the temperature used in standard conditions to decrease the likelihood of mispriming. The annealing temperature can be raised to a temperature that will still allow enough priming events for the amplification to occur. For instance, if a primer has a melting temperature of 50° C., and an annealing temperature of 45° C. would be chosen under standard conditions, an annealing temperature of 50° C. would thus be more stringent then 45° C. For example primers of the type $dT_{16}VN$ can lead to strong mispriming under normal RT conditions and therefore decrease the specificity of the cDNA pools synthesized (Mizuno et al., 1999). Analogous results have been reported for AMV and HIV-1 reverse transcriptase. Primer promiscuity can be decreased by increasing temperature during annealing and reverse transcription. For this purpose thermostable enzymes can be used that exhibit reverse transcriptase activity or reverse transcriptase enzymes can be thermo protected by adding thermo protectants such as trehalose to the reaction (Carninci et al., 1998). An added benefit of using trehalose is that the amount of full length cDNA increases (Carninci et al., 1998). This property was also described by Spiess et al. (2002). In addition Spiess showed that betaine can also increase the amount of full length cDNA and that a combination of betaine and trehalose gave the best result (Spiess et al., 2002). Such RT can be derived from moloney murine leukemia virus (M-MLV) (U.S. Pat. No. 4,943,531 A) or in a more preferred embodiment M-MLV lacking RNAse H activity (U.S. Pat. No. 5,405,776 A). Yet another possibility to raise primer specificity is to include competitive oligo nucleotide blockers as described by Mizuno et al. (1999). Therefore the present invention also comprises a method wherein high stringency conditions are used for the processes of reverse transcription and/or the amplification.

Preferably, in the method according to the invention the selectivity of the reverse transcription and/or amplification reaction, in particular the polymerase chain reaction, is increased by the utilization of trehalose, betaine, tetramethylammonium chloride, tetramethylammonium oxalate, formamide and oligoblockers, or by the utilization of dimethylsulfoxide during the polymerase chain reaction, to reduce the occurrence of mispriming and increase the amount of full length cDNA.

As all reverse transcriptases have a high error rate it is preferred that a proofreading activity is included in the reaction. Enzymes that have such an activity through their 3'→5' exonuclease function are e.g. polymerases such as PFU, Ultma, Vent, Deep Vent, PWO and Tli, or E. coli. exonuclease III. In addition to reducing errors introduced into a cDNA during the RT the inclusion of a proofreading activity can also enhance full length cDNA synthesis (Hawkins, 2003).

It is further preferred that such a proofreading activity is also included in the PCR step of the method. On the one hand this will reduce errors introduced into the sequence during PCR as well as extend the size of cDNA molecules that can be amplified (Barnes, 1994). As such a 3'→5' exonuclease activity can degrade primers used in the reaction it is preferred to protect primers from degradation, e.g. by introducing a phosphorothioate bond at the 3' terminal of the primer (Skerra, 1992; Di Giusto, 2004) or by using LNAs (locked nucleic acids).

It is preferred that during reverse transcription and/or PCR, enzymes or enzyme combinations are used that have a high processivity and fidelity.

The present invention provides a method for full transcriptome coverage and no redundancy at least in principle. However, methodical properties such as mispriming and polymerase stop can influence the outcome nevertheless. Coverage of long mRNAs therefore depends on the used enzymes. Proof reading enzymes, used for long PCR methods, enlarge the scope of transcriptome coverage to at least 99% under ideal conditions for the given enzymes and method parameters (e.g. long extension times). Misanealing, which can be minimized by e.g. stringency and proof reading activities, may lead to a limited redundancy of the covered transcriptome.

The maximal length of an RNA molecule that can be displayed depends in particular on the quality of the reverse transcription and the amplification reaction, e.g. PCR. In principle long PCR can amplify DNA up to at least 35 kb (Barnes., 1994) and RT-PCR up to at least 20 kb (Thiel et al., 1997), so at least 99.9% of all transcripts can be displayed. However there exist exceptional long RNA molecules such as titin (NCBI accession number X90568) that has about 80 kb length and even though in theory displayable, for practical reasons one will probably not tune the display to such transcripts.

Preferably, the reverse transcription is performed by a reverse transcriptase (RT) derived from the moloney murine leukemia virus, AMV, HIV-1, HIV-2, wherein the RNase H activity of these RTs is or is not present or is reduced. Reverse transcription can be performed by any enzyme that has a reverse transcriptase activity, e.g. Tth DNA polymerase that exhibits reverse transcriptase activity in the presence of $Mn^{2+}$. In addition the RNA can be degraded after the reverse transcription step, for example by an RNA degrading enzyme such as RNase to facilitate long PCR.

Preferably for reverse transcription as well as the amplification designed enzymes can be used, which are independent of a thermal cycling procedure, i.e. are capable of isothermal polymerisation.

It is further preferred that primers used for reverse transcription have a wobble in one or more bases, preferably 1, 2, 3, 4 or 5 bases, on their 3' end preferable between position 2 to 4 upstream of the last dT of the terminal dT stretch to further increase specificity.

As used herein, the term "primer" refers to a mixture of oligonucleotides that have the same sequence.

As used herein, the term "wobble primer" refers to a mixture of oligonucleotides that have the same sequence, except for the base or bases that are part of the "wobble".

As used herein, the term "wobble" refers to a base within a primer pool that is present as a mixture of two or three or four different nucleotides.

As an example a wobble primer can consist of oligonucleotides of the sequence ACACACN, where N is referred to as the wobble and N is A or C or T or G. This wobble primer would then consist of a mixture of nucleotides of the sequence ACACACA, ACACACC, ACACACT and ACACACG.

When using N nucleotides as a mixture (N is a mixture of dA, dC, dG and dT) in wobble primers, nucleotides with universal bases can be used instead, such as deoxyinosine, 3-nitropyrrole 2'-deoxynucleoside and 5-nitroindole 2'-deoxynucleoside. Universal bases will basepair with any nucleotide (dA, dC, dG, dT).

Therefore, according to the invention the primers used for reverse transcription or amplification preferably have a wobble substitution, e.g. dT may be substituted by dG, dA, dC and vice versa, in one or two bases on their 3' end, preferably between position 2 and 4 upstream of the last nucleotide, which is preferably dT for a 5' RT primer (for 5'→3' strand synthesis) and a 3' amplification primer and dA for a 5' amplification primer. In the PCR step of the method such "wobble" primers can be used to increase specificity for both the 5' and 3' end of the cDNA molecules to be amplified.

Wobbles can also be used to anchor the primer that is complementary to the (e.g. poly A) tail of the original RNAs to the bases immediately upstream of the tail. In this case the selection into different pools can be achieved by primers selective to bases corresponding to bases after the cap of the original RNA. The same rational can be applied to the 3' end of the cDNA where wobbles can anchor a primer to the bases corresponding to bases downstream of the cap of the original RNA. Therefore the selection into different pools would be done through primers that select for bases that correspond to bases immediately upstream of the (e.g. poly A) tail of the original RNAs.

Even further preferred is a method according to the invention, wherein the wobble base represents a substitution by universal bases, preferably deoxyinosine, 3-nitropyrrole 2'-deoxynucleoside or 5-nitroindole 2'-deoxynucleoside, which can basepair to any regular nucleobase such as dA, dT, dG or dC.

In a preferred embodiment specificity of the cDNAs amplified can be enhanced by using a combination of a primer that is exonuclease resistant on its 3' end (e.g. by including a phosphorothioate modification or a locked nucleic acid) with a 3'→5' exonuclease function, such an activity being a property of e.g. Pfu DNA Polymerase. This will provide an "off switch" for amplification if a single mismatch, or multiple mismatches occur in the first 8 bases from the 3' end of the primer. (Yang et al., 2005). As the bases at the 3' prime end of the primers are the ones that discriminate the cDNA pools in methodologies presented in this invention, it is preferred that such an "off switch" is included to stop the extension of primers that mismatched to a cDNA, thus further enhancing specificity. Preferably in the inventive method a polymerase sensitive for a mismatch between nucleotides of the primer and the RNA or cDNA is used (either during reverse transcription or amplification), and the polymerase does not extend a mismatched exonuclease resistant primer, wherein it is preferred that the primers are resistant to exonucleases, especially preferred by a phosphorothioate modification or a locked nucleic acid.

In a preferred embodiment the primer used for reverse transcription consists of an oligo dT stretch or tail complementary stretch without an anchor. Since the selection of specific RNAs occurs on the cDNA level via the amplification step described above, specificity (of the anchor) at the RT level is not a necessity. Of course mispriming should be avoided, especially where the (oligo T) primer aligns with the sequence upstream of the (poly A) tail stretch of the RNA. Mispriming can be avoided using stringent conditions and/or using an enzyme with proof reading properties. Preferably the annealing temperature during the RT process lies in the range of 30 to 50° C., depending on the melting temperature of the primer used.

Even though utilization of stringent conditions, such as the use of higher annealing temperatures, wobbled primers and oligoblockers, can decrease mispriming events during reverse transcription (RT), a preferred solution is to not separate into different pools during RT. As the reverse transcriptase reaction allows for more mispriming sequences to be extended than the amplification reaction (e.g. PCR reaction), it is most preferred that the separation into pools is done during the amplification reaction. This also decreases the RT reactions necessary to one per sample to be displayed.

In a preferred embodiment the generation of full-length cDNA can be further advanced. Under non optimal conditions reverse transcriptase might stop polymerisation and/or fall off the RNA strand before reaching the 5' end of the RNA molecule. Generally this is attributed to secondary structure that has not melted and that the polymerase cannot traverse. Therefore generating also partial cDNA's. To lower the probability that such transcripts will interfere with subsequent (PCR) amplification one can exploit the intrinsic ability of reverse transcriptase to add a few ($Mn^{2+}$ and $Mg^{2+}$ dependent 1-6 nucleotides, Schmidt et al., 1999) dC once it reaches the 5' cap end of the mRNA molecule (Clark, 1988). The cap (Furuichi et al., 1975) structure greatly increases the nontemplated nucleotide adding capability of RT compared to mRNAs that do not have the cap structure. This can be used to further enrich for full-length cDNAs. In a subsequent PCR reaction cDNAs can be selected that have these Cs present by including dG nucleotides in the 5' primer at the complementary position. In such a case the tailing can be done with any nucleotide except dC, preferably with dT or dA. The general structure of a 5' PCR primer that would select for cDNAs that have three Cs added to their 5' end, then will be $dT_xdGdGdGHN_y$ or $dA_xdGdGdGHN_y$ or $dC_xdGdGdGHN_y$; H can either be dA or dC or dT.

In a preferred embodiment the method according to the invention, includes the generation of cDNA with a 3' sequence of oligo-dC, preferably with a length of 1 to 6 dC nucleotides, during reverse transcription, dependent on a 5' cap of the template RNA or mRNA.

Preferably the ability of a reverse transcriptase to generate the 3' sequence of oligo-dC is increased by the addition of $Mn^{2+}$ ions during the process of reverse transcription. The number of nucleotides added can be increased by including Mn ions in the RT reaction as described in Schmidt et al., 1999. Therefore in a preferred embodiment Mn ions are included in the RT reaction to increase quantitatively the nontemplated addition of dC on the 3' end of cDNA in a cap dependent manner. Subsequent tailing is carried out with any nucleotide but dC in order to allow the selection of the cap dependent dC. The selection of added nucleotides during tailing can be done by providing just the wanted nucleotide during this process. One primer that is used for (PCR) amplification can therefore have the general formula $dP_xdG_yHN_z$; $P_x$ representing nucleotides complementary to the tail; dG being deoxyguanylate and y an integer between 0 and 10, preferably between 1 and 5 more preferable between 3 and 5; H can either be dA or dC or dT; and N is a sequence of nucleotides, its members independently selected from either dA, dC, dG, dT; z is an integer between 0 and 10 preferably between 0 and 5.

In a preferred embodiment the cap dependent 3' sequence of oligo-dC is used to isolate fully transcribed cDNA by using a second primer during the amplification which is specific for the oligo-dC sequence. This can be done by using a primer as described above.

Preferably the tailing of the 3' end of the cDNA is performed with a polynucleotide sequence, which is characterized by the absence of dC.

Even more preferred the DNA polymerase used for the amplification reaction is Taq DNA polymerase, Tfl DNA polymerase, aTaq DNA polymerase, Sequenase or Klentaq.

In special embodiments an enzyme with proof reading activity is used, preferably selected from PFU, Ultma, Vent, Deep Vent, PWO and Tli polymerases and E. coli. exonuclease III, is used during the amplification reaction. Such an enzyme can be used in addition to a polymerase, preferably in lower concentrations than the polymerase, or, if it is a polymerase itself, instead. Polymerases with proof reading activity prevent stops during DNA polymerisation and ensure long transcripts with significantly reduced errors. Preferably a combination of such an enzyme with proof reading capability is used with a polymerase above.

In a more preferred embodiment a primer used for the amplification reaction, which is preferably a polymerase chain reaction, is characterized by the general formula $dP_xdG_yHN_z$, wherein $P_x$ represents nucleotides complementary to the tail added to the 3' end of the cDNA, e.g. by the terminal transferase or by the template switching property of the reverse transcriptase or by any other means, dG being deoxyguanylate and y an integer, including 0, preferably between 2 and 5, H being either dT or dA or dC, N being a sequence of nucleotides with a length z wherein its member nucleotides are independently selected from dA, dC, dG and dT, and z being an integer between 0 and 10, preferably between 0 and 5.

The 5' end of primers used for RT and PCR can also be anchored to any sequence that will allow RT and PCR to be carried out. 5' and 3' PCR primers may have different melting temperatures and PCR conditions may be optimized by equalizing melting temperatures of primer pairs through the addition of an anchor to one or both of the primers. For certain downstream application it might also be of benefit to add a specific sequence such as a promoter that can start RNA Polymerase transcription (e.g. T7 or T3), or the inclusion of a restriction site.

In a most preferred embodiment the amplification is performed by PCR and the PCR primers contain anchoring sequences, which allow proper placement at the end of the 3' or 5' oligonucleotide end stretch of the cDNA.

Preferably an amplification primer or a reverse transcription primer contains a promoter for RNA polymerases. This optional feature allows the transcription of the cDNA and its PCR products.

Preferably the promoter enhances transcription by the T7, T3 or SP6 RNA polymerase.

Primers as well as PCR products can be labeled by any reporter group known in the art that enables their detection. Examples of reporter groups include fluorescent, chemiluminescent or radioisotopes and others known in the art. Any reporter group can be used that can be detected by such techniques as fluorescent measurement, light emission measurement, scintillation counting and other means known in the art.

Accordingly, the amplification primers and/or the amplification products are labeled by a reporter group, preferably fluorescence markers, chemiluminescence markers or radioisotopes in a preferred embodiment of the present invention. Preferably, these reporter groups are used to detect the DNA.

Recently, it has been shown that during transcription at least some eukaryotes such as *Arabidopsis* (Jin et al., 2004) can add arbitrary nucleotides to RNA molecules on their 3' end immediately before the poly A tail, in most cases one or two. And even within a certain gene such nucleotide additions can be heterogenic. Therefore using a set of primers that discriminate for the first and/or second base upstream of the poly A during reverse transcription the intended pooling of a mRNA species into certain pools of cDNA will fail for certain transcripts. However a higher degree of pooling can be achieved using nucleotides upstream of these arbitrarily added nucleotides for the primers that define the fractions. A preferred primer for reverse transcription and PCR amplification that will be complementary to the poly A tail and select for bases above these additions be of following general structure $dT_xVN_yM_z$, where dT depicts deoxythymidylate with x repetitions; V and N are wobble bases where V is either dA, dC or dG; N is a sequence of dA, dC, dG, dT, independently selected for each member; y is an integer equal to or greater than 0, preferable between 1 and 5, and M is either dA, dC, dG, dT; z is an integer above 1, preferably between 1 and 10. In such a primer $M_z$ will specify the cDNA pool to be amplified. As the number of nucleotides added to RNA molecules before polyadenylation might differ even for a specific transcript, a primer can be a mixture of oligonucleotides where the amount of y in N is different. An additional benefit is that in order for the Polymerase to be able to extend the chain the pressure for correct hybridization of bases after the wobble will strongly increase, therefore decreasing mispriming of the bases that define the fractions that will be amplified, hence specificity will be increased.

In a preferred method according to the invention arbitrary nucleotides, preferably one to three nucleotides, are added to the 3' end of the RNA or mRNA posttranscriptionally but before the addition of a (e.g. poly A) tail, and the primers for reverse transcription and/or PCR contain a sequence with a wobble corresponding to the arbitrary sequence.

A simplified version of the invention that will not specifically select for full length cDNA can be formulated by not using the 3' (dC) nontemplated adding function of the RT enzyme. There will still be a portion of full length cDNAs that have no dC added under normal RT condition. Tailing and PCR can be used as described to selectively amplify pools of cDNA. Each cDNA will still be present in exactly one pool. However the extent of PCR products present that will correspond to full length RNA molecules will be determined by the quality of the RT reaction alone. As one does not select in the PCR reaction that follows for full length cDNA copies, more than one cDNA molecule might give rise to PCR products that represent a single RNA molecule, therefore introducing redundancy. Still each RNA molecule will be represented at least once. Redundancy can be minimized by employing methods that favour full length reverse transcription, such as addition of trehalose and/or betaine and/or increasing temperature as disclosed above. Even though redundancy might not be abolished in this embodiment, still each RNA molecule will be present at least once. This is an improvement compared to other DD techniques that can reach a representation for a certain mRNA molecule only statistically.

Also there exist species of RNA molecules that do not have a poly A tail and a cap structure. However such RNA molecules will also have 5' and 3' prime end that can be used during subsequent amplification to enrich for defined fractions as is intended by this invention.

Examples of RNA that may or may not have a cap and may have or may not have a poly A tail are non protein coding RNAs (ncRNA) such as ribosomal RNA (rRNA), transfer RNA (tRNA), micro RNA (miRNA), small interfering RNA (siRNA), piwi-interacting RNA (piRNA) and small nuclear RNA (snRNA).

In RNA molecules that do not have a poly A tail, a tail such as a poly A tail, is added synthetically (e.g. enzymatically) prior to reverse transcription. Preferably a polynucleotide tail is added where the nucleotides are selected independently from A or C or G or U.

There exist species of RNA that have a certain size range, such as miRNA that are about 19 to 23 bases long. Therefore size separation of pools of amplification products derived from miRNAs is limited. When displaying miRNAs with a size range of 19 to 23 bases, a maximum of 5 molecules per pool can be resolved according to size. Therefore a quite large primer set (primer matrix) has to be used to resolve all miRNA molecules.

Figure 6:
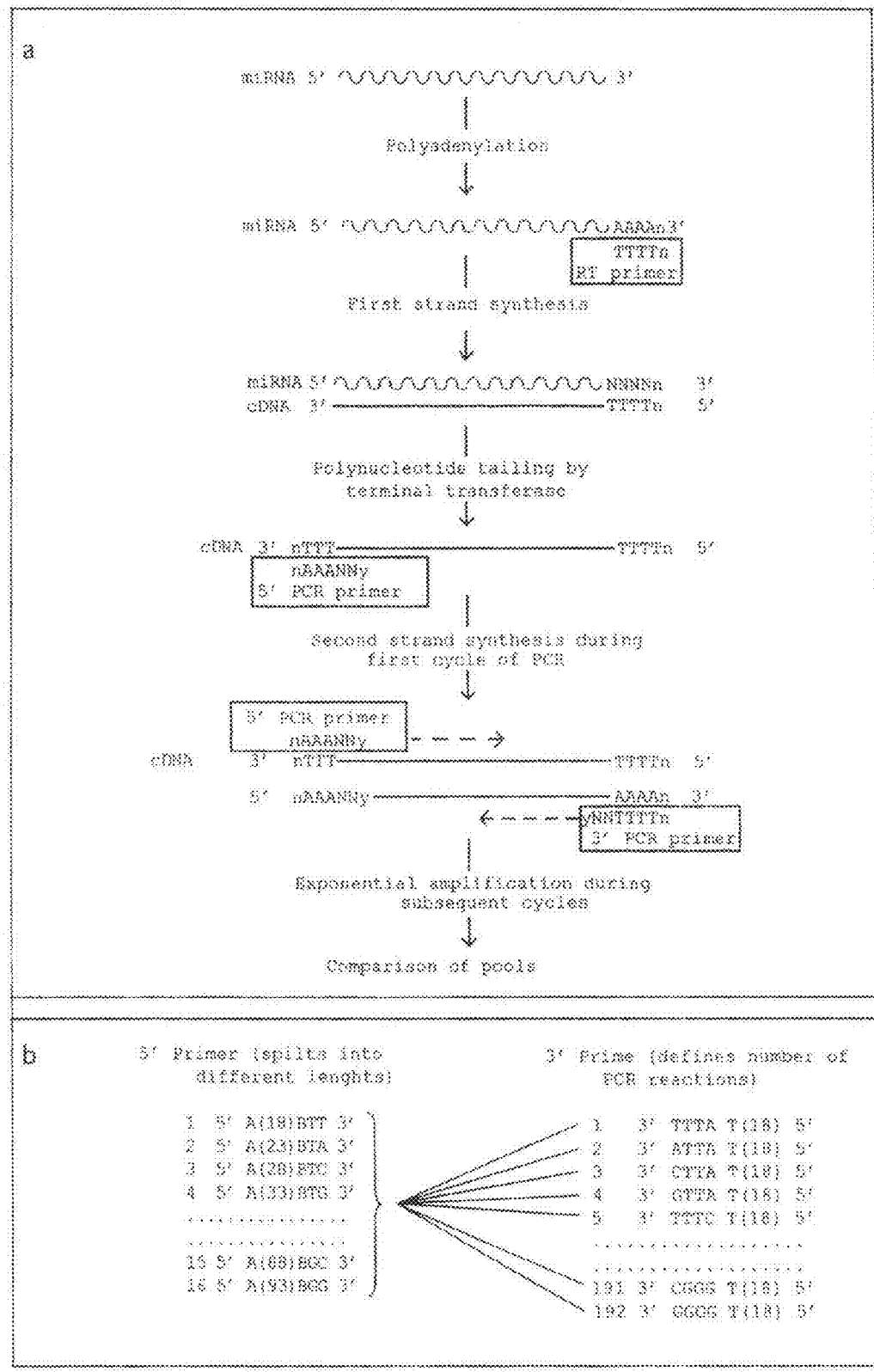

In an alternative approach the nucleotides of one end of the miRNA can be used to artificially enlarge the amplification products for a specific number of nucleotides according to the terminal sequence of the miRNA. A general formula of such a primer is $P_xN_y$; with P representing nucleotides complementary to a tail; N represents nucleotides independently selected from either A, C, G, T; y is an integer between 0 and 10; x defines the number of nucleotides and is different for all $N_y$. If the 5' end of the miRNA is used for such a size enlargement, a primer mix containing certain or all possible 5' primers is used in combination with a 3' primer that is selective for nucleotides at the end of the miRNA molecule, to define a certain pool. One possible primer matrix according to the principles of this invention is shown in FIG. 6.

Therefore in a preferred embodiment of the invention, amplification products—in particular full length amplification products—are generated that are differentially enlarged by certain numbers of nucleotides depending on the 5' or 3' sequences of the RNA or the full length cDNA.

Preferably, amplification products are generated that are differentially enlarged by defined numbers of nucleotides at their 5' and/or 3' end as compared to the RNA, by using different primers which have different lengths and recognize different 5' or 3' end sequences of the RNA or the full length cDNA. Also, pools of amplification products can be generated that are enlarged by defined numbers of nucleotides at their 5' and or 3' end as compared to the RNA, preferably by using as a 5' and/or as a 3' primer a mixture of primers, where each primer recognizes a different end sequence and has a different length. Preferably the primers have a defined sequence that is not complementary to the cDNA (during the amplification step) or RNA (during the reverse transcription step).

In prokaryotes mRNA has no poly A tail. Methods have been devised (Amara et al., 1997) that can make full-length cDNA from such molecules, such as adding a synthetic poly A tail. It is also within the scope of this invention to apply said methods to such molecules.

Preferably in a method according to the invention RNA or mRNA samples are used, which do not have a poly A tail or a tail sequence and, preferably a polynucleotide tail, especially preferred a poly A tail, is added synthetically (enzymatically) prior to reverse transcription.

To decrease the necessary amount of RNA to perform the display a preamplification step can be introduced before the amplification reaction, e.g. the PCR. Whether or not separation into pools was done in the reverse transcription (RT) step, the preamplification step has to be designed in a way that will amplify all the cDNA that is intended to be separated into defined pools in the amplification (PCR) step. The preamplification step can be introduced before the tailing or after the tailing, before the main amplification with the specific primers.

For example a promoter such as T7 RNA Polymerase can be added to the 5'-end of the primer that is used for priming the RT reaction. After the RT and before the amplification (PCR) RNA can be synthesized by an RNA polymerase specific to the promoter, for example T7 RNA polymerase. Such obtained amplified RNA has to be reverse transcribed again and depending whether or not a sequence is present downstream of the cDNA base that is complementary to the first base of the RNA and that can be used to prime the amplification reaction (PCR) on this end, such a sequence has to be added, for example by the template switching ability of the reverse transcriptase or by tailing with terminal deoxynucleotidyltransferase.

Another example for a preamplification step is the use of a preamplification PCR. In case of a terminal deoxynucleotidyltransferase tailed cDNA one primer has to be specific to the so added tail. For example a poly T tailed cDNA will need a primer such as $dA_x$ and a primer complementary to the poly A tail of the original RNA for example $dT_x$. Preferably one can preamplify only full length cDNA by including variable amounts of G, preferably between 1 and 5, to enable the primer to hybridize only to cDNA that was fully reverse transcribed and thus where the reverse transcriptase added Cs through its non templated nucleotide adding capacity in a cap dependent manner. Additionally the primer that can hybridize to the sequence complementary to the original RNA poly A tail can be anchored to the 5'-end of the poly A tail by including one or more wobbles. This will help to increase the length of the amplification (PCR) products obtained, by not needlessly amplifying long stretches of poly A tail. Such a primer has the general formula of $dT_xVN_y$ (x is the amount of dT, V either G, C or A, and N any nucleotide).

The discrimination of the cDNA into different pools can also be accomplished by using more than one amplification (PCR) step. Each amplification (PCR) step would be more specific to the pool to be amplified. For instance in a first amplification (PCR) a primer such as $dT_x$ could be used for hybridizing to cDNA on the side that is complementary to the poly A tail side of the RNA. This primer would be not discriminating. In a next step, 3 reactions could be used with one being primed with $dT_xG$, one with $dT_xA$ and one with $dT_xC$. Thus creating 3 pools. In another PCR step the pools can be further divided. For example the $dT_xG$ pool can be divided in to 4 pools by priming with $dT_xGA$, $dT_xGC$, $dT_xGG$ and $dT_xGT$. Thus creating a total of 12 pools. The same rational can be applied to the other end of the cDNA and the pooling of both sides can be combined if desired. Such a sequential pooling can on the one hand further decrease the amount of starting material (RNA) needed or help to achieve a pooling tuned to the complexity of the sample to be investigated or the depth the investigator wants to cover.

It is within the scope of the invention that two or more samples of RNA that are combined by methods that yield normalization or subtraction between such RNA or their derived cDNA or PCR products can also be displayed according to disclosed methods. For example RNA can be (pre) treated by reducing RNA species in high concentration.

Therefore the present invention also relates to a method wherein the RNA in the sample or the cDNA is preamplified, preferably by PCR, or wherein RNA samples are normalized or subtracted. These (pre)treatment steps are preferably introduced before the main (discriminating) amplification c).

In a further embodiment of the method according to the invention the step of fractionation of the amplification product is performed by gel electrophoresis, pulsed-field electrophoresis, agarose gel electrophoresis, PAGE, capillary electrophoresis or pulsed-field capillary electrophoresis. Fractionation and comparison of samples generated during PCR can be done by any methods that allow distinguishing DNA molecules according to specific properties, such as sequence or size. Such methodologies include e.g. gel electrophoresis, such as polyacrylamide gel electrophoresis (PAGE). Especially suited is capillary gel electrophoresis because of its high resolving power and because many samples can easily be analyzed in parallel (Behr et al., 1999). Standard capillary electrophoresis machines today can process 384 samples in one run. And through the use of appropriate protocols one can achieve the necessary resolving power over a wide range of sizes. Especially long fragments can be resolved sufficiently with pulsed-field capillary electrophoresis (Heller et al., 2001; Morris et al., 2001). Also methods have been devised to collect fractions of the molecules separated in a capillary (Irie et al., 2000; Magnusdottir et al., 2001). Such fractions that represent transcripts of interest (e.g. differentially expressed genes) can then be subjected to further analysis, such as sequencing, to determine the identity of the molecule.

In a preferred embodiment the detection of differences between two cDNA pools can be included into the PCR step of the method. Such methodologies, that can measure DNA levels and/or the change of such levels during PCR, are generally referred to as "real time PCR" (e.g. Wittwer et al. 1997a, Wittwer et al. 1997b). One procedure applicable measures fluorescence from SYBR Green I dye, that has been added to the PCR reaction. This dye will show a strong increase in fluorescence when intercalating with double stranded DNA. The more DNA present in the reaction the stronger the fluorescence. Therefore providing the means to calculate the amount of DNA present in the reaction. The measurement is usually done at the end of the polymerization step as the products will be double stranded. As the amount of DNA increases during subsequent cycles, so will the fluorescence. This data can be compared e.g by blotting on a curve and curves can be compared between different samples. If there is only one cDNA amplified the curve will have an exponential phase. By comparing the start of the exponential phase between samples one can calculate relative amounts of DNA. If two or more products will be present in a given sample, curves will add onto each other and will result in a change of steepness. Still such data can be compared between different samples, if the cDNA pool amplified is not too complex. It is preferred that the amount of cDNAs amplified in one PCR reaction is reduced to such a point that differences in amplification of each product can still be detected. Another way of analysing a sample, when using real time PCR, is the possibility of calculating a melting curve of the DNA present at the end of each cycle. Each PCR product present in the reaction will melt at a specific temperature, that is defined by the sequence. As a product is melting into its single strands the dye is not intercalating with DNA anymore, whereby a drop of fluorescence will result. Products that will melt at different temperatures will be represented as an increase and then a decrease of the steepness at different areas of the melting curve. Comparing curves between cycles and different samples of the same cDNA pool to be amplified, one can identify samples with a different profile. A melting curve analysis can also be done only at the end of the PCR, however differences in products that have plateaued might not be detected.

The use of such analysis methods preferably in an automated procedure can rapidly screen for samples that show differences during or at the end of PCR and eliminate the need to analyse all of them through a fractionation procedures such as gel electrophoresis.

Therefore in a preferred embodiment the detection of differences between two cDNA pools, preferably corresponding pools between two or more samples, is done during or at the end of the amplification step, preferably being a PCR step, of the method, preferably by real time PCR.

Clearly the methods described in this invention can be integrated into a partially or fully automated process. For example the size fractionation, comparison of different samples, collection of fractions, and sequencing can be all done on a chip. The technologies have already been demonstrated in principle (Xie et al., 2001).

Such an integration of the method onto a chip can also be done for the PCR step of the method. It is preferred that the primers, or primer pairs are spotted and/or bound onto a solid support to enable solid phase DNA amplification (e.g. by PCR). Through microarraying or nanoarraying or single molecule arraying the whole set of primers onto a solid support, a single reaction vessel can be created that contains the whole primer matrix or parts thereof. Therefore instead of using an own reaction vessel for each 5'-3' primer pair, a single reaction vessel contains all 5'-3' primer pairs. It is preferred that each primer pair is located in a defined area.

A primer matrix can also be created where each 5'-3' primer pair is bound onto its own solid support (e.g. a bead) and the solid support itself is then arranged in such a manner that each primer combination or primer pair can be addressed independently. For instance a matrix of beads can be arranged randomly in microwells and the location of each bead decoded by methods known to the art (e.g. Gunderson et al., 2004). The method as described by Gunderson can thus be adapted and incorporated by the present invention. This method requires only a few labels and several sequential hybridizations to identify thousands of different DNA sequences with great accuracy. Regarding the primer matrix, the primers on the areas may comprise the information for decoding themselves (e.g. as sequence which can be decoded by other labeled oligo nucleotide by several steps of hybridisation, detection and washing) or together with the primers of the invention decoding oligonucleotides can be bound onto the carrier.

Therefore in a preferred embodiment a 5'primer or a 3'primer or a 5'-3' primer pair is spotted and/or bound onto a solid support, preferably the spot or the solid support is located in a defined 2-dimensional or 3-dimensional area and it is preferred that such an area contains information to decode the identity of the primer or primer pair located in that area.

In a preferred embodiment the primer matrix is generated by direct on chip synthesis of the 5' primers or 3' primers or 5'-3'primer pairs.

In a preferred method according to the invention the steps of reverse transcription and amplification are performed in one step.

It is obvious to the one skilled in the art that other possibilities exist to enrich for full-length cDNA. Such methods can easily be adapted to amplify subsequently pools of full length cDNA that are defined through nucleotides that are complementary to the 5' end and/or nucleotides on the 3' end upstream of the poly A tail.

For example the CapSelect method (Schmidt et al., 1999) can be used to substitute the steps of reverse transcription and tailing the 3' end of the cDNA. This method is also drawn on the nontemplated addition of C nucleotides of reverse transcriptase, and addition of a poly N tail, preferably a poly A tail. However the poly A tail consists of ribonucleotides instead of deoxyribonucleotides as it is claimed that terminal transferase will preferably add only 3 to 4 ribonucleotides, compared to an unspecified amount of deoxyribonucleotides. This is important for the method as in a next step an adaptor will be specifically linked to the 3' end of the cDNA selecting for 3'-AAACCC-5'. Using a primer that is complementary to this adaptor and a primer complementary to the poly A tail it is intended to amplify full length cDNA. Instead of using universal primers to amplify all cDNAs one can use sets of primers that select for the 5' and/or 3' nucleotides and will amplify pools of cDNAs. The primer structure for hybridizing to the poly A tail and selecting for x amount of bases before the poly A tail will be the same as described. For amplifying the 5' end of mRNAs one can use the adaptor sequence followed by 3 to 4 Ts and 3 to 4 Gs and an x amount of bases that correspond to the 5' sequence of the RNA transcripts. Increasing x will decrease the number of transcripts amplified through such a primer.

Preferably the polynucleotide tail added by the terminal transferase consists of ribonucleotides, preferably 2 to 6 ribonucleotides, preferably adenosine or thymidine, after a 3' sequence of oligo-dC, preferably with a length of 1 to 6 dC nucleotides, which is generated during reverse transcription, dependent on a 5' cap of a template RNA or mRNA, and the second amplification primer (5' primer) comprises complementary nucleotides to the ribonucleotides and oligo-dCs and 1 to 10 nucleotides upstream of the olio-dC sequence.

The method for amplification of certain cDNAs, derived from mRNA, can also be used to determine the expression level of individual mRNAs. Preferably for measuring the expression level of messenger RNA a method according to the invention is employed, including the separation and/or identification of amplification results. Like in common DD results of certain cell lines can be compared for better visualisation of different expressions.

Furthermore the present invention provides a kit for a method according to the invention comprising a DNA polymerase, preferably Taq polymerase, a reverse transcriptase or mixtures of different polymerases, cofactors or salts of metal ions, preferably $Mg^{2+}$ and $Mn^{2+}$, requested by a polymerase, primers and optionally a terminal transferase and additional buffer substances. The primers are preferably selective for the 5' and 3' end of a RNA or cDNA as described above. Even more preferred the primers of the primerset are selective for the first, second, third, fourth and/or fifth terminal nucleotide of the RNA or cDNA (of either end, independently from each other). Preferably the kit comprises 1, 2, 3, 4, 5, 10, more than 10, more than 20 or more than 30 primer pairs. With this kit a display method according to the invention can easily and quickly be performed. Preferably instructions for the execution of the method are also included. Preferably the full primerset (primer matrix) or parts thereof—preferably one of each primer pair—are bound to a solid support such as a chip, preferably a glass chip.

In another aspect of the present invention there is provided a solid surface, preferably a chip, in particular preferred a glass chip, comprising in defined areas, preferably in spots, a pair of primers, wherein different primers are selective for at least two, preferably at least three, even more preferred at least four, most preferred at least 10, different 3' or 5' end sequences of target polynucleotides, preferably selected from RNA or cDNA, and each area comprises primers for at least two different end sequences (e.g. a pair of a 5' and a 3' primer), preferably one primer is selective for a (e.g. poly A) tail or a complement thereof and even more preferred selective for the next 1 to 10 nucleotides, preferably the next 1, 2, 3 or 4 nucleotides (of either the 5' and/or the 3' primer. The primers can be specific as described above. These primers may also, e.g. in these combinations, be used in the kit or the method. A primer pair in one area selective for mRNA is specific for the poly A tail and the 5' (cap) end, as well as the next 1 nucleotide (different in each area). Preferably the solid surface comprises at least two, at least 4, at least 10, at least 20 or at least 40 different primer pairs.

Provided is further a solid surface, preferably a chip, in particular preferred a glass chip, comprising in defined areas, preferably in spots, a 5' primer and a 3' primer or a pair of primers, wherein the primers are as defined above being specific for both ends of a cDNA or a RNA, especially comprising formula $dP_xdG_yHN_z$; in particular preferred the solid surface comprises at least two, more preferred at least 9, especially preferred at least 20, most preferred at least 60, different areas with different primers or primer pairs.

Also provided is a solid surface, preferably a chip, in particular preferred a glass chip, comprising in defined areas, preferably in spots, a 5' primer or a 3' primer comprising the general formula as defined above ($dP_xdG_yHn_z$) or a complement thereof, preferably selected from a primer comprising one of the following sequences:
SEQ ID NO. 21: AGA GAT TTT TTT TTT TTT TT GA,
SEQ ID NO. 22: AGA GAT TTT TTT TTT TTT T GG,
SEQ ID NO. 23: AGA GAT TTT TTT TTT TTT T GC,
SEQ ID NO. 24: AGA GAT TTT TTT TTT TTT TT GT,
SEQ ID NO. 25: AGA GAT TTT TTT TTT TTT TT CA,
SEQ ID NO. 26: AGA GAT TTT TTTTTT TTT TT AG,
SEQ ID NO. 27: AGA GAT TTT TTT TTT TTT TTT AA,
SEQ ID NO. 28: AAA AAA AAA AAA AAA GGG ATA,
SEQ ID NO. 29: AAA AAA AAA AAA AAA GGG ACA,
SEQ ID NO. 30: AAA AAA AAA AAA AAA GGG AGA,
SEQ ID NO. 31: AAA AAA AAA AAA AAA GGG AAA,
SEQ ID NO. 32: AAA AAA AAA AAA AAA GGG GTA
SEQ ID NO. 33: GTA, AAA AAA AAA AAA AAA GGG CTA,
SEQ ID NO. 34: AAA AAA AAA AAA AAA GGG TTA,
in particular preferred the solid surface comprises at least two, more preferred at least 9, especially preferred at least 20, most preferred at least 60, different areas with different primers or primer pairs.

In a further aspect a method for amplifying a pool of polynucleotide molecules in a sample is provided, comprising the steps of:
a) obtaining (or providing) a sample of RNA and reverse transcription of entire RNA molecules thus creating full length cDNA or obtaining (or providing) a sample of full length cDNA,
b) tailing the 3' end of the transcribed cDNA with a polynucleotide tail after the 3' end,
c) amplification of the cDNA using a pair of primers, wherein a first (3') primer is specific for the 5' end of the cDNA and a second (5') primer is specific for the upstream portion of the polynucleotide tail and the next 1 to 100 nucleotides, preferably the next 1 to 50 nucleotides, especially preferred the next 1 to 20 nucleotides, in particular preferred the next 1 to 10 nucleotides (i.e. nucleotide 1, 2, 3, 4, 5, 6, 7, 8, 9 or 10), upstream of the 3' polynucleotide tail of the cDNA, preferably also comprising unspecific wobble nucleotides, especially preferred in the upstream portion within the 1 to 100 nucleotide range—wherein at least 1, 2, 3, 4, 5, 6, 7, 8, 9 or 10 nucleotide(s) is/are specific for a nucleotide of the cDNA; the method further preferably defined as given above.

The method preferably includes the use of a primer, which is specific for a 3' tail of the RNA (optionally an added 3' tail) or mRNA (preferably the endogenous 3' poly A tail) and the next 1 to 100 nucleotides, preferably the next 1 to 50 nucleotides, especially preferred the next 1 to 20 nucleotides, in particular preferred the next 1 to 10 nucleotides (i.e. nucleotide 1, 2, 3, 4, 5, 6, 7, 8, 9 or 10), upstream of the 3' tail is used for the reverse transcription and/or a first amplification primer is specific for a 5' tail of the cDNA, which is complementary to the 3' tail of the RNA or mRNA, and the next 1 to 100 nucleotides, preferably the next 1 to 50 nucleotides, especially preferred the next 1 to 20 nucleotides, in particular preferred the next 1 to 10 nucleotides (i.e. nucleotide 1, 2, 3, 4, 5, 6, 7, 8, 9 or 10), downstream of the 5' tail. Of course, also both or independently from one another, in the 5' and the 3' primers, the nucleotide stretch (1 to 100 nucleotides) next to the tail (or tail complement) may comprise unspecific nucleotides (such as wobble nucleotides) in addition to at least 1, 2, 3, 4, 5, 6, 7, 8, 9, 10 or more specific nucleotides selecting for different pools (with or without pool separation) of the amplification product. Such primers can also of course be used for the reverse transcription as well. Products of such wobble primers (where any nucleotide may be present at a corresponding position to the wobble position) still fulfil the requirement of full-length cDNA or full-length amplification product although the sequence may not be preserved at positions that correspond to the unspecific nucleotide positions. Using longer unspecific nucleotide primer stretches primer-loops may occur thus resulting in a product with an altered length which is however still considered to be equivalents to full-length cDNA or amplification products for the present invention.

The present invention is further illustrated by the following example and figure without being limited thereto.

FIG. 1 shows a graphical representation of a procedure using the principles of the present invention to amplify full length cDNA into defined subpopulations. The oligo-T and oligo-G stretches indicated in the primers are terminal anchors of the primers and the N, NN and $NN_y$ indicate nucleotides selected from A, T, G, C for defining the subpopulations.

Figure 2:
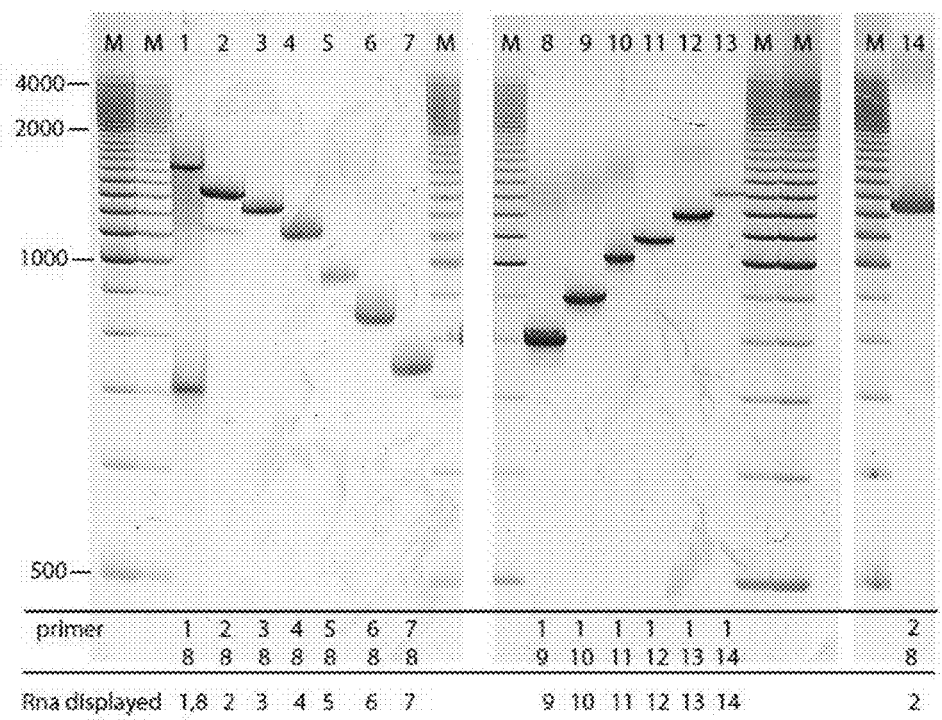

FIG. 2: Gel electrophoresis product of a display of a pool of artificial mRNA molecules according to example 2: In lane 1-7 primer nr. 8 was used together with primers nr. 1-7. In lanes 8-13 primer nr. 1 was used together with primers 9-14.

Figure 3:
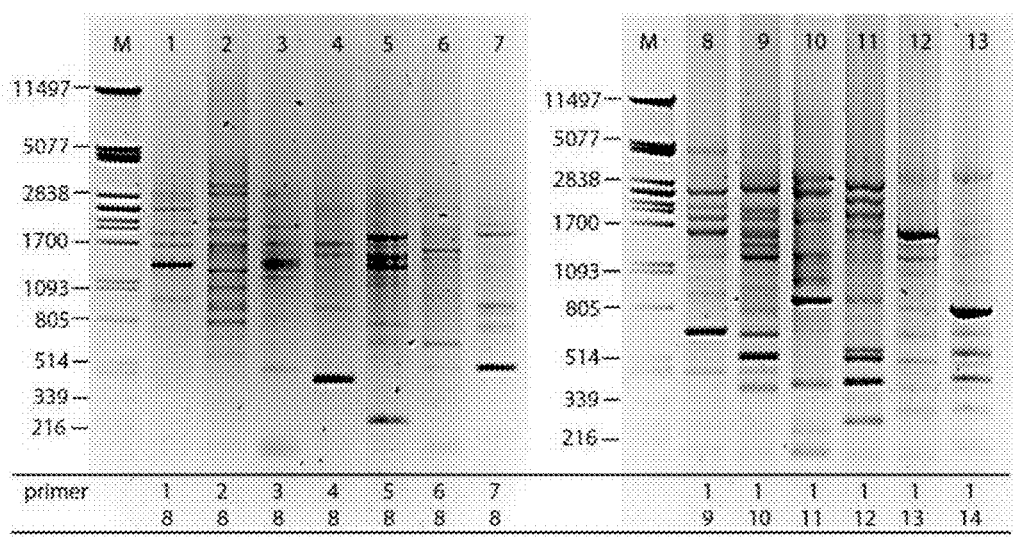

FIG. 3: Gel electrophoresis product of an organised full length expression display of mouse liver RNA according to example 3.

Figure 4:
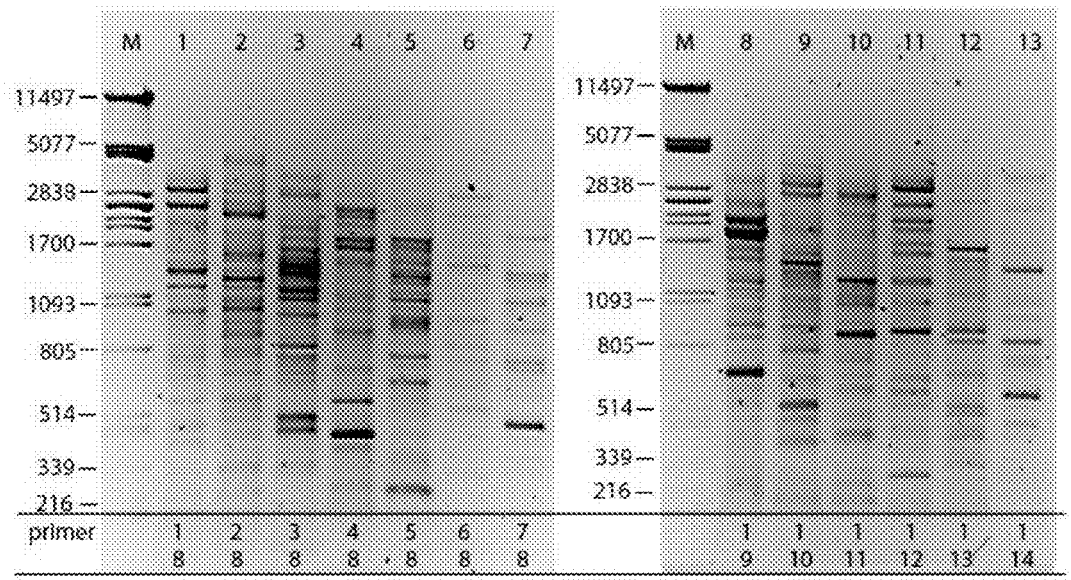

FIG. 4: Gel electrophoresis product of an organised full length expression display of mouse liver RNA according to example 4 with PCR preamplification.

Figure 5:
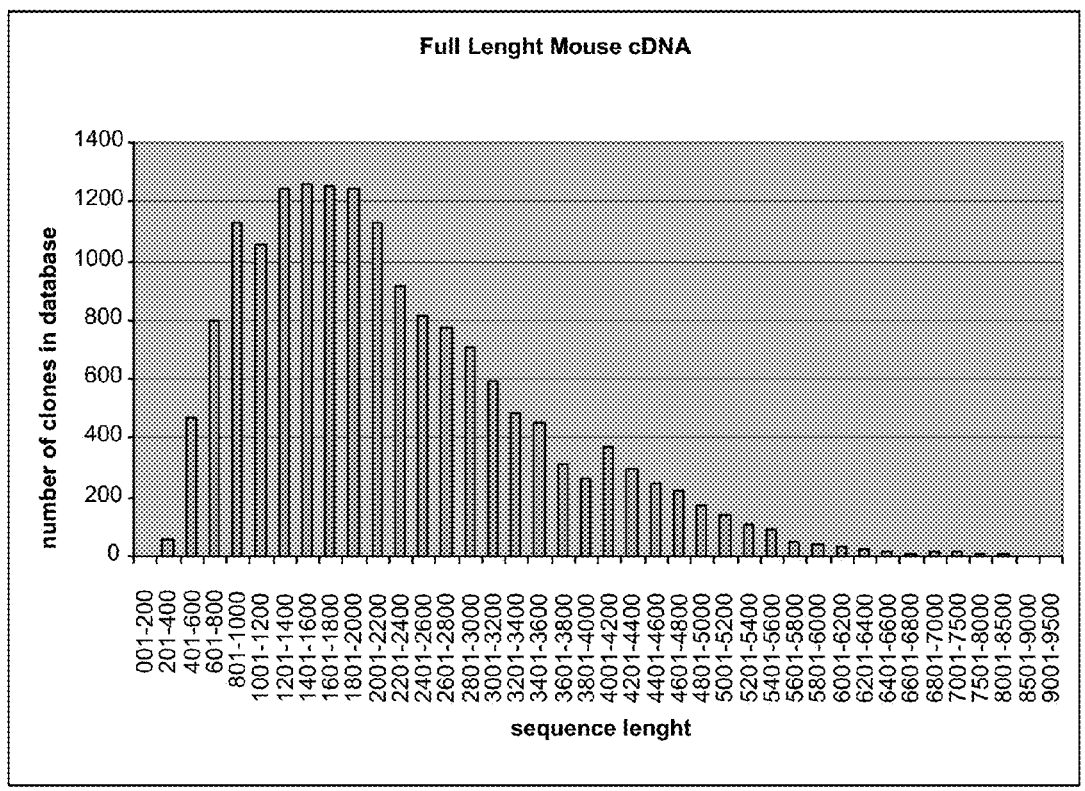

FIG. 5: NCBI nucleotide database screening for non redundant full length mouse cDNA clones. 99% of the 16854 clones present in the database are between 200 and 6000 bases in length and 99.9% below 7500 bases and no clone was above 9500 bases.

FIG. 6 shows how RNA without a cap and a tail, such as miRNA, is divided into subpopulations. a) Steps of the procedure. Primer nomenclature as in FIG. 1 b) One possible Primer matrix that increases the resolving power by increasing the size range of the amplification products. The B in the 5' primers indicate a mixed base (wobble) that is selected from T, G, C.

EXAMPLES

Example 1

Principle of Procedure

An overview of an example of a polynucleotide amplification procedure according to the present invention is given in FIG. 1. Anchored primers for reverse transcription can follow the formula $dT_xV$ or $dT_xVN_y$ (with x defining a repetition of deoxythymidylate ("dT") that has in combination with the V or $VN_y$ part a high enough specificity and melting temperature to successfully prime the RT reaction; V is either deoxyguanylate ("dG"), deoxyadenylate ("dA") or deoxycytidylate ("dC"); N is a sequence of y nucleotides selected independently from dA, dC, dG or dT; if more than one base is used for anchored primers y defines their number; increasing y will increase the subpopulations of reverse transcripts. The tailing of the 3' end of such synthesized cDNA with a poly N tail can be done using terminal transferase—N stands for a sequence of uniformly nucleotides selected from dT, dA, dC or dG, independently form the "N" indicated in the reverse transcription primers. The amplification of the cDNA pools, optionally preselected by the $VN_y$ stretches defined by polymerase chain reaction (PCR) is performed using primers that hybridize to the 5' and 3' end of the cDNA by selecting to terminal sequences like the nucleotides appended by the terminal transferase (3' of the cDNA; corresponding to the 5' end of the original mRNA) and the poly T stretch (5' of the cDNA; complementary to the 3' poly A tail of the original mRNA) and selecting for an oligo $dN_y$ sequence, wherein N is a stretch of several nucleotides, again independently selected from dT, dA, dC or dG and define different mRNA populations through y bases immediately adjacent to the tails.

Example 2

Amplification of all the RNA Molecules Present in a Sample

As all the mRNA molecules present in a sample are not known, even in well characterized tissues such as liver from human or mouse, and their number maybe in the thousands, an approach was chosen to use a pool of 14 artificially synthesized mRNA molecules to show that all RNA molecules present in that sample are detected. For this purpose stretches with different lengths of genomic DNA from the mouse GAPDH gene (GenBank Accession: NC_000072) were amplified by standard PCR. 5' primers were used that had an anchored T7 polymerase promoter. Following the promoter a combination of 4 bases were included that would define each mRNA on its 5' end. Primers chosen for the 3' end included, after the GAPDH specific sequence, a combination of 4 bases, that would define these molecules upstream of the poly A tail. Following these 4 bases 21 dT or in one of the RNAs 22 dT were included for the poly A tail. The PCR products obtained were gel purified and subjected to standard T7 RNA transcription, that included 7-methyl-guanosine (the cap). Such T7 reaction products were again gel purified. A mixture of such obtained synthetic mRNA molecules was used as starting material for the reverse transcription (RT). To show that the methods disclosed are specific for the 5' as well as 3' end of the mRNA molecules, 7 of the 14 molecules had a fixed sequence on the 5' end and varied in the 3' end and 7 molecules had a fixed sequence on the 3' end and varied at the 5' end. For sequence of the resulting artificial mRNA molecules see table 1.

Reverse transcription was carried out in a 25 µl reaction consisting of 50 mM Tris-HCl (ph 8.3), 75 mM KCl, 3 mM MgCl$_2$, 10 mM DTT, 0.6M trehalose, 2M betaine, 0.5 mM dATP, 0.5 mM dTTP, 0.5 mM dCTP, 0.5 mM dGTP, 40 nM primer (oligo dT$_{(21)}$). The artificial mRNA mix was included at a level of about 4 ng/µl reaction volume. The reaction (without the RT) was heated to 70° C. for 20 sec, 32° C. for 2 min. Then the Molony Murine Leukemia Virus Reverse Transcriptase lacking RNase H activity (M-MLV RT (−H)) was added a concentration of 4-8 units/µl reaction volume and the reaction continued for 2 min at 32° C. At this point 0.5 U of Pfu polymerase was added. Four cycles at 50° C. for 10 min and 60° C. for 10 sec were used to fully reverse transcribe the RNA, after that the reaction was cooled to 4° C.

TABLE 1

Sequences of artificial RNAs to be displayed

| Primer Nr. | 5' sequence . . . 3 sequence | | Length of RNA | Predicted Length of PCR product |
|---|---|---|---|---|
| 1 | $^{m7}$G AT AT CCG CCC TGT GCT . . . SEQ ID NO. 6 | CTG TGG GCA AGG TC TC A$_{(21)}$ SEQ ID NO. 7 | 1515 | 1531 |
| 2 | $^{m7}$G AT AT CCG CCC TGT GCT . . . SEQ ID NO. 6 | TGT CCC TTT TGG TC CC A$_{(21)}$ SEQ ID NO. 8 | 1333 | 1348 |
| 3 | $^{m7}$G AT AT CCG CCC TCT GCT . . . SEQ ID NO. 6 | TTG TGG AAG GGC TC GC A$_{(21)}$ SEQ ID NO. 9 | 1243 | 1258 |
| 4 | $^{m7}$G AT AT CCG CCC TGT GCT . . . SEQ ID NO. 6 | CGA TGC CCC CAT TC AC A$_{(21)}$ SEQ ID NO. 10 | 1112 | 1128 |
| 5 | $^{m7}$G AT AT CCG CCC TGT GCT . . . SEQ ID NO. 6 | CAC CAC CAT GGA TC TG A$_{(21)}$ SEQ ID NO. 11 | 942 | 958 |
| 6 | $^{m7}$G AT AT CCG CCC TGT GCT . . . SEQ ID NO. 6 | CAA CGG GAA GCC TC TA A$_{(21)}$ SEQ ID NO. 12 | 843 | 859 |
| 7 | $^{m7}$G AT AT CCG CCC TGT GCT . . . SEQ ID NO. 6 | ACG ACC CCT TCA TC TT A$_{(21)}$ SEQ ID NO. 13 | 736 | 753 |
| 8 | $^{m7}$G AT AT GAT GCG CAA AGG . . . SEQ ID NO. 14 | TCC TGC GGC CCA TC TC A$_{(21)}$ SEQ ID NO. 35 | 687 | 703 |
| 9 | $^{m7}$G AC AT GGC CTA AGC AAG . . . SEQ ID NO. 15 | TCC TGC GGC CCA TC TC A$_{(21)}$ SEQ ID NO. 35 | 786 | 802 |
| 10 | $^{m7}$G AG AT GAG CAC GGA AGC . . . SEQ ID NO. 16 | TCC TGC GGC CCA TC TC A$_{(21)}$ SEQ ID NO. 35 | 880 | 896 |
| 11 | $^{m7}$G AA AT CCG CTT TGA TTT . . . SEQ ID NO. 17 | TCC TGC GGC CCA TC TC A$_{(21)}$ SEQ ID NO. 35 | 994 | 1010 |
| 12 | $^{m7}$G GT AT CAG CTC CCC ATC . . . SEQ ID NO. 18 | TCC TGC GGC CCA TC TC A$_{(21)}$ SEQ ID NO. 35 | 1070 | 1086 |
| 13 | $^{m7}$C CT AT GGG CCT GGG TCA . . . SEQ ID NO. 19 | TCC TGC GGC CCA TC TC A$_{(21)}$ SEQ ID NO. 35 | 1178 | 1194 |
| 14 | $^{m7}$C TT AT GGG CGG AGT GGA . . . SEQ ID NO. 20 | TCC TGC GGC CCA TC TC A$_{(21)}$ SEQ ID NO. 35 | 1287 | 1303 |

The cDNA was phenol/chloroform extracted, ethanol precipitated and dissolved in 10 µl of H$_2$O. Poly T tailing was carried in a 20 µl reaction containing 0.2 mM dTTP, 100 mM cacodylate buffer (pH 6.8), 1 mM CoCl$_2$, 0.1 mM DTT and 15 units of terminal deoxynucleotidyl transferase for 15 min at 37° C. The reaction was Phenol/Chloroform extracted, ethanol precipitated and dissolved in 100 µl H$_2$O.

PCR was carried in a 10 μl reaction containing 2.5 μl tailed cDNA, 50 mM Tris (pH 8.8), 14 mM $(NH_4)_2SO_4$, 4 mM $MgCl_2$, 0.2 mM of each dNTP, 0.2 μM of each primer (table 2, FIG. 2), 0.5 units Taq polymerase and 0.03 units Pfu polymerase. Samples were denatured at 93° C. for 30 sec, and cycled 21 times at 93° C. for 10 sec, 55° C. for 30 sec, 72° C. for 10 min. The initial annealing temperature of 55° C. was decreased each cycle by 0.5° C. min. Thereafter followed 19 cycles at 93° C. for 10 sec, 49° C. for 30 sec, 72° C. for 10 min with a final extension step at 72° C. for 2 min.

TABLE 2

PCR primers

| Primer nr. | | |
|---|---|---|
| 1 | SEQ ID NO. 21 | AGA GAT TTT TTT TTT TTT TT GA |
| 2 | SEQ ID NO. 22 | AGA GAT TTT TTT TTT TTT T GG |
| 3 | SEQ ID NO. 23 | AGA GAT TTT TTT TTT TTT T GC |
| 4 | SEQ ID NO. 24 | AGA GAT TTT TTT TTT TTT TT GT |
| 5 | SEQ ID NO. 25 | AGA GAT TTT ITT TTT TTT TT CA |
| 6 | SEQ ID NO. 26 | AGA GAT TTT TTT TTT TTT TT AG |
| 7 | SEQ ID NO. 27 | AGA GAT ITT TTT TTT TTT TTT AA |
| 8 | SEQ ID NO. 28 | AAA AAA AAA AAA AAA GGG ATA |
| 9 | SEQ ID NO. 29 | AAA AAA AAA AAA AAA GGG ACA |
| 10 | SEQ ID NO. 30 | AAA AAA AAA AAA AAA GGG AGA |
| 11 | SEQ ID NO. 31 | AAA AAA AAA AAA AAA GGG AAA |
| 12 | SEQ ID NO. 32 | AAA AAA AAA AAA AAA GGG GTA |
| 13 | SEQ ID NO. 33 | AAA AAA AAA AAA AAA GGG CTA |
| 14 | SEQ ID NO. 34 | AAA AAA AAA AAA AAA GGG TTA |

2.5 μl of the reaction product was added to 2.5 μl 100% formamide loading buffer and denatured at 96° C. for 2 min and cooled on ice, loaded on a 3.5% acrylamide, 7M urea gel and run at 180V for 2 h and subsequently silver stained.

The results can be seen in FIG. 2. In lane 1-7 primer nr. 8 was used together with primers nr. 1-7. In lanes 8-13 primer nr. 1 was used together with primers 9-14. In each lane the PCR amplified the specific product, as the predicted length of the PCR products shown in table 1 perfectly matches the lengths of the products on the gel.

The primer combination in lane 1 amplifies the 2 specific products corresponding to the RNA to be displayed. The reaction carried out in lane 1 is the most demanding reaction of the set as two products have to be amplified, the ones representing RNA 1 and 8. In addition as can be seen in table 1 the RNA molecules were designed in a way to enhance miss priming of the PCR reaction represented in lane 1. All RNA molecules (except RNA Nr. 6) have on position 3 and 4 before the T tail the same bases as on position 1 and 2 of RNA number 1 and 8. As primer nr. 1 uses its last two bases to select the cDNA to be amplified, it potentially can miss prime with any of the other cDNA present in the sample. And as cDNA molecules 1-8 have the same bases on its other end it is only the two last bases of primer 1 that selects between these 8 molecules in reaction 1. However only the two RNAs to be amplified are displayed, showing the great specificity that can be reached in such a display.

Lane 2 shows the limits of this reaction. In addition to the band to be amplified a faint band that corresponds to RNA nr. 4 was amplified. However the band to be amplified is several times more intense than the band that resulted through the miss priming event. Additionally even though a touch down protocol was used for the thermal cycling, the same profile was used for all the different primer combinations. To show that in principle the reaction can be optimized for a specific primer set another reaction was carried that included 1.302M betaine and 1.3% DMSO. The product is shown in lane 14 and only the correct band is displayed.

Example 3

Amplification of Total RNA from Mouse Liver

Total RNA (13 μg) from mouse liver was reverse transcribed, tailed and PCR amplified under the same conditions as for the whole artificial RNA set in example 2.

The same conditions for RT, tailing and PCR were used to show that it is possible to display RNA molecules from a complex mixture under the same stringent conditions as it is possible with artificial RNA. The PCR products were run on a 0.7% agarose gel to resolve longer molecules. As can be seen in FIG. 3 each primer combination amplifies a unique profile.

The length distribution of the RNA molecules displayed in FIG. 3, matches very well the length distribution of cDNA in the NCBI nucleotide database screening for non redundant full length mouse cDNA clones (FIG. 5).

As on averaged about 10-15 bands can be seen on each lane the full set of 768 primer combinations ($3 \times 4^4$) displays about 7680-11520 PCR products representing full length RNA molecules expressed in liver. Being able to resolve such profiles on a simple 0.7% agarose gel shows the power of the method and the ease, with what it can be performed in the laboratory.

Example 4

Utilization of PCR Preamplification Step

Preamplification was carried out in a 10 μl reaction containing 2.5 μl of a purified tailed cDNA generated as in example 3, 50 mM Tris (pH 8.8), 14 mM $(NH_4)_2SO_4$, 4 mM $MgCl_2$, 0.2 mM of each dNTP, 0.2 μM of Primer $dT_{(21)}$, 0.2 μM of Primer $dA_{(21)}$, 0.5 units Taq polymerase and 0.03 units Pfu polymerase. Samples were denatured at 93° C. 30 sec, and cycled 11 times at 93° C. 10 sec, 42° C. 30 sec, 72° C. 11 min with a final extension step at 72° C. for 2 min. This reaction was diluted to 1 ml by adding 990 μl $H_2O$. 2.5 μl of this dilute was used in the following PCR using the same PCR conditions as in example 3 with the difference that the final 2 cycles where omitted. As can be seen in FIG. 4 a distinctive banding can be seen for each primer combination. The preamplification step as used in the example shows that 500 ng of total RNA are enough to provide material for even a large display with 768 reactions per RNA sample, as might be needed to resolve highly complex RNA mixtures from tissues like brain. The amount of RNA used can easily be reduced by increasing the cycles during preamplification. Therefore the sensitivity of the display should meet even the most demanding applications, where only limited amounts of RNA are available. Furthermore the amount of bands per primer pair has increased compared to example 3. As the high annealing temperatures used in the discriminating PCR step, in both example 3 and 4, exert an extremely high stringency, some low level transcripts might be just below the detection limit when no preamplification step is used.

Example 5 miRNA Display

An overview of an example of a polynucleotide amplification procedure according to the present invention, where the RNA has no cap and no poly A tail, in this case microRNA (miRNA), is given in FIG. 6.

To be able to reverse transcribe full length cDNA from miRNA that has no Poly A tail, a synthetic tail is added by using poly A polymerase. In a second step the Poly A tailed RNA is reverse transcribed into cDNA using an oligo dT primer. After polynucleotide tailing of the cDNA by terminal transferase, the cDNA samples have sufficient long nucleotide terminals that allow for primers to anneal and amplify the cDNA sequences into different pools according to the 5' and 3' sequences of the original miRNA molecules (FIG. 6a).

As microRNA (miRNA) molecules have a size of about 19-23 bases, a sufficiently large primer matrix (all possible combinations of 5' and 3' primers) has to be used to separate all miRNAs into different pools where differences in expression between samples can be measured.

Alternatively one end of the miRNA sequence can be used to artificially enlarge the amplification products for a specific number of nucleotides according to the terminal sequence of the miRNA. FIG. 6b shows an example of such a matrix. In this case the 5' primer is used to split miRNA amplification products into different lengths according to the second and third nucleotide of the miRNA. In cases where the comparison of different pools is done by an additional size fractionation (such as capillary gel electrophoresis) all 16 5' primers of FIG. 6b can be used as a primer mix. This 5' primer mix together with one 3' primer defines a pool. Therefore 192 pools have a similar resolution when compared to 192×16=3072 pools, where each 5' primer would be used together with each 3' primer.

REFERENCES

Amara et al., 1997, Nucleic Acids Res. 25, 3465-3470.
Barnes, 1994, PNAS 91, 2216-2220.
Behr et al., 1999, Electrophoresis 20, 1492-1507.
Carninci et al., 1998, Proc. Natl. Acad. Sci. U.S.A 95, 520-524.
Clark, 1988, Nucleic Acids Res. 16, 9677-9686.
Di Giusto et al., 2004 Nucleic Acids Res. 32, e32 1-8.
Frohman et al., 1988, Proc. Natl. Acad. Sci. U.S.A 85, 8998-9002.
Furuichi et al., 1975, Nature 253, 374-375.
Gunderson et al., 2004 Genome Res. 14, 870-877.
Hawkins et al., 2003, Biotechniques 34, 768-773.
Heller et al., 2001, Methods Mol. Biol. 162, 293-305.
Irie et al., 2000, Electrophoresis 21, 367-374.
Jin et al., 2004, RNA. 10, 1695-1697.
Kovarova et al., 2000, Nucleic Acids Res. 28, e70i-e70iii.
Liang et al., 1992, Science 257, 967-971.
Magnusdottir et al., 2001, Methods Mol. Biol. 162, 323-331.
Matz et al., 1997, Nucleic Acids Res. 25, 2541-2542.
Mizuno et al., 1999, Nucleic Acids Res. 27, 1345-1349.
Morris et al., 2001, Methods Mol. Biol. 162, 307-321.
Prashar et al., 1996, Proc. Natl. Acad. Sci. U.S.A 93, 659-663.
Prashar et al., 1999, Methods Enzymol. 303, 258-272.
Rebagliati et al., 1985, Cell 42, 769-777.
Schmidt et al., 1999, Nucleic Acids Res. 27, e31.
Spiess et al., 2002, Anal. Biochem. 301, 168-174.
Skerra, 1992, Nucleic Acids Res. 20, 3551-54.
Thiel et al., 1997, Anal. Biochem. 252, 62-70.
Welsh et al., 1992, Nucleic Acids Res. 20, 4965-4970.
Wittwer et al., 1997a, Biotechniques 22, 130-138.
Wittwer et al., 1997b, Biotechniques 22, 176-181.
Xie et al., 2001, Methods Mol. Biol. 162, 67-83.
Yang et al., 2005, Biochem. Biophys. Res. Commun. 328, 265-272.

The invention claimed is:

1. A method for amplifying a pool of polynucleotide molecules comprising the steps of:
    obtaining a RNA;
    reverse transcribing the RNA using one or more reverse transcription primers, thereby creating a full length cDNA or obtaining a full length cDNA;
    adding a polynucleotide tail at a 3' end of the full length cDNA;
    amplifying the full length cDNA using a pair of amplification primers, wherein the amplification primers comprise a first 3' amplification primer that hybridizes to a 5' end of the full length cDNA, and a second 5' amplification primer that hybridizes to both at least a part of the polynucleotide tail and a part of the cDNA, wherein the second 5' primer hybridizes to one to ten nucleotides upstream of the 3' polynucleotide tail of the cDNA.

2. The method according to claim 1, wherein the step of adding a polynucleotide tail is performed by using terminal transferase.

3. The method according to claim 1, wherein the step of amplifying the full length cDNA is performed by PCR.

4. The method according to claim 1, further comprising the step of separating the one or more amplified products.

5. The method according to claim 1, further comprising the step of identifying or sequencing the one or more amplified products.

6. The method according to claim 1, wherein the RNA comprises total RNA, total mRNA, purified RNA, purified mRNA, or any combinations thereof from a specimen.

7. The method according to claim 1, wherein the reverse transcription primers or the first 3' primer or the second 5' primer has a wobble base substitution positioned in one or two bases on the 3'end.

8. The method according to claim 1, wherein the step of reverse transcribing generates a 3' oligo-dC on the full length cDNA and is dependent on a 5' cap of the RNA.

9. The method according to claim 1, wherein the step of adding a polynucleotide tail is performed by a polynucleotide sequence in absence of dC.

10. The method according to claim 1, wherein the RNA or the full length cDNA is preamplified, or wherein the RNA is normalized or subtracted.

11. The method according to claim 1, wherein the first 3' primer and the second 5' primer comprise the formula $dP_x dG_y HN_z$, wherein $P_x$ represents nucleotides complementary to the polynucleotide tail, wherein dG is deoxyguanylate, wherein y is an integer, wherein H is dT or dA or dC, wherein N is a sequence of nucleotides with a length z having nucleotides independently selected from dA, dC, dG and dT, and wherein z is an integer between 0 and 10.

12. The method according to claim 1, wherein the step of amplifying the full length cDNA is performed by PCR and the amplification primers comprise anchoring sequences capable of allowing proper placement at a 3' or 5' end of the cDNA.

13. The method according to claim 1, further comprising the step of differentially enlarging the one or more amplified products by defined numbers of nucleotides at the 5' or 3' end compared to the RNA, or by using different primers having different lengths recognizing different 5' or 3' end of the RNA or the full length cDNA.

14. The method according to claim 1, further comprising the step of spotting a 5' primer or a 3' primer or a 5'-3' primer pair-onto a solid support.

15. The method according to claim 1, wherein the steps of reverse transcribing a RNA and the step of amplifying a full length cDNA are performed in a single step.

16. A method for amplifying a pool of polynucleotide molecules in a sample comprising the steps of:
    obtaining a RNA and reverse transcribing the RNA thereby creating a full length cDNA or obtaining a full length cDNA;
    adding a polynucleotide tail on a 3' end of the full length cDNA,
    amplifying the full length cDNA using a pair of primers comprising
    a first 3' primer that hybridizes to a 5' end of the full length cDNA; and
    a second 5' primer that hybridizes to at least a part of the polynucleotide tail and also that hybridizes to a region between 1 to 100 nucleotides upstream of the polynucleotide tail.

17. The method according to claim 1, wherein the reverse transcription primers comprise at least one primer specific for 1 to 100 nucleotides upstream of the 3' tail of the RNA or an endogenous 3' poly A tail of the RNA.

18. The method according to claim 1, wherein the first 3' primer is specific for 1 to 100 nucleotides downstream of a 5' tail of the full length cDNA, wherein the 5' tail of the full length cDNA is complementary to a 3' tail of the RNA.

19. The method according to claim 1, wherein the one or more reverse transcription primers comprise at least one primer specific for a 3' poly A tail of the RNA.

20. The method according to claim 1, wherein the first 3' amplification primer is specific for a 5' poly-T stretch of the full length cDNA and is complementary to 1 to 10 nucleotides downstream of the 5' poly-T stretch wherein the 5' poly-T is complementary to a 3' poly A tail of the RNA.

21. The method according to claim 7, wherein the wobble base substitution is between position 2 and 4 upstream of the last nucleotide.

* * * * *